US009039946B2

(12) United States Patent
Fischer et al.

(10) Patent No.: US 9,039,946 B2
(45) Date of Patent: May 26, 2015

(54) REVERSIBLY THERMOCHROMIC COMPOSITIONS

(75) Inventors: Walter Fischer, Reinach (CH); Abdel-Ilah Basbas, Basel (CH); Mara Destro, Bologna (IT); Manuele Vitali, Bologna (IT); Dario Lazzari, Bologna (IT); Mirko Rossi, San Lazzaro di Savena (IT)

(73) Assignee: BASF SE, Ludwigshafen (DE)

( * ) Notice: Subject to any disclaimer, the term of this patent is extended or adjusted under 35 U.S.C. 154(b) by 1651 days.

(21) Appl. No.: 11/921,604

(22) PCT Filed: May 31, 2006

(86) PCT No.: PCT/EP2006/062749
§ 371 (c)(1),
(2), (4) Date: May 14, 2009

(87) PCT Pub. No.: WO2006/131465
PCT Pub. Date: Dec. 14, 2006

(65) Prior Publication Data
US 2009/0302284 A1    Dec. 10, 2009

(30) Foreign Application Priority Data

Jun. 10, 2005  (EP) ..................................... 05105099
Nov. 11, 2005  (EP) ..................................... 05110655

(51) Int. Cl.
| | |
|---|---|
| C07C 69/95 | (2006.01) |
| C07D 209/58 | (2006.01) |
| C07D 307/77 | (2006.01) |
| C07C 317/24 | (2006.01) |
| C07C 323/52 | (2006.01) |
| C09K 9/02 | (2006.01) |
| C07C 317/44 | (2006.01) |
| C07C 323/22 | (2006.01) |

(52) U.S. Cl.
CPC ............... *C07C 69/95* (2013.01); *C07C 317/24* (2013.01); *C07C 317/44* (2013.01); *C07C 323/22* (2013.01); *C07C 323/52* (2013.01); *C07C 2103/44* (2013.01); *C07D 209/58* (2013.01); *C07D 307/77* (2013.01); *C09K 9/02* (2013.01); *C09K 2211/1011* (2013.01); *C09K 2211/1029* (2013.01)

(58) Field of Classification Search
CPC .... C07C 69/95; C07C 317/24; C07C 323/52; C07C 323/22; C07C 317/44; C07C 2103/44; C07D 209/58; C07D 307/77; C09K 9/02; C09K 211/1029; C09K 2211/1011

USPC ................. 552/200, 201; 252/602; 514/680
See application file for complete search history.

(56) References Cited

U.S. PATENT DOCUMENTS

| | | | | |
|---|---|---|---|---|
| 4,033,923 | A | * | 7/1977 | Tsujimoto et al. ............ 524/160 |
| 4,036,805 | A | * | 7/1977 | Tsujimoto et al. ............ 524/242 |
| 4,826,550 | A | * | 5/1989 | Shimizu et al. ............... 156/166 |
| 5,177,227 | A | * | 1/1993 | Fischer et al. ................ 552/201 |
| 5,281,570 | A | | 1/1994 | Hasegawa et al. ............ 503/216 |
| 5,300,663 | A | * | 4/1994 | Fischer et al. ................ 552/202 |
| 5,354,869 | A | | 10/1994 | Langhals et al. ............. 548/453 |

FOREIGN PATENT DOCUMENTS

| | | | | |
|---|---|---|---|---|
| DE | 659638 | | 4/1938 | |
| GB | 1601945 | | 11/1981 | |
| JP | S61-136965 | * | 7/1986 | ............ C08L 101/04 |
| SU | 665218 | * | 5/1979 | ............ G01K 11/12 |

OTHER PUBLICATIONS

Rath et al. Journal of Physical Chemistry A 2001 vol. 105 pp. 7945-7956.*
Russel and Young Journal of the American Chemical Society 1966 vol. 88 No. 9 pp. 2007-2014.*
Russell et al. Organic Magnetic Resonance 1969 vol. 1 pp. 125-137.*
SciFinder Substance Identifier printed Apr. 30, 2014 2,2,6,6-tetramethyl-4-hydroxypiperidine.*
USPTO Partial Translation SU 665218 performed and sent Apr. 30, 2014.*
Sigma-Aldrich Product Data (Sigma-Aldrich Product Data (ID # 536834, Bis(2,2,6,6-tetramethyl-4-piperidyl) sebacate, Printed Sep. 19, 2014; {http://www.sigmaaldrich.com/catalog/product/aldrich/535834?lang=en&region=US}).*
USPTO Partial Translation JP S61-163965 Printed Sep. 19, 2014.*
Chemical Abstract 82:87790 for JP 49080143, Aug. 1972.
Chemical Abstract 82:74575 for JP 49080142, Aug. 1974.
G. Russell et al., Organic Magnetic Resonance, (1969), vol. 1, pp. 125-137.
C.-Y. Li et al., Electrochimica Acta, vol. 25, pp. 1135-1142 (1980).
Ch. Weizmann et al., J. Chem. Soc. (1939), pp. 398-401.
Von Paul Tunmann et al., Arzneimittel-Forschung, vol. 11, (1961), pp. 474-476.

* cited by examiner

*Primary Examiner* — Patrick Ryan
*Assistant Examiner* — Aaron Greso
(74) *Attorney, Agent, or Firm* — Oblon, McClelland, Maier & Neustadt, L.L.P.

(57) ABSTRACT

The present invention pertains to a reversibly thermochromic system comprising a substituted or an unsubstituted 6,11-dihydroxy-naphthacene-5,12-dione and a base and to a reversibly thermochromic composition comprising the reversibly thermochromic system and a carrier material and to novel substituted 6,11-dihydroxy-naphthacene-5,12-diones.

13 Claims, No Drawings

REVERSIBLY THERMOCHROMIC COMPOSITIONS

The present invention pertains to a reversibly thermochromic system comprising a substituted or an unsubstituted 6,11-dihydroxy-naphthacene-5,12-dione and a base and to a reversibly thermochromic composition comprising the reversibly thermochromic system and a carrier material and to novel substituted 6,11-dihydroxy-naphthacene-5,12-diones.

EP 0438376 A1 relates to 6,11-diaryloxy-naphthacene-5,12-diones in photochromic systems. Several substituted 6,11-dihydroxy-naphthacene-5,12-diones are used as starting material for the preparation of 6,11-diaryloxy-naphthacene-5,12-diones.

6,11-Dihydroxy-naphthacene-5,12-diones are described in several publications: U.S. Pat. No. 4,033,923, DE 659638; GB 1601945; CAN 82:87790 of JP49080143; CAN 82:74575; Russell et al., Organic Magnetic Resonance, 1969, Vol. 1, pp. 125-137; Li et al., Electrochimica Acta, vol. 25, pp. 1135-1142; Weizmann et al., J. Chem. Soc., 1939, pp. 398-400; and Tunmann et al., Arzneimittelforschung 11, 1961, pp. 474-476.

Known reversible organic thermochromic systems consist of a basic color former such as a leuco dye and an acidic developer such as a phenolic compound. In cold, these components are a dark colored salt and upon heating they dissociate above a certain temperature. On cooling the dark colored salt forms again. The major drawbacks are the poor photostability of the basic color former and the acidic developer and the color change may be retarded and such systems have a reduced thermal stability which is a disadvantage in plastic articles prepared by extrusion.

The system according to this invention does not have these disadvantages as the used compounds may have a greater photostability and less or no retarding of the color change. For instance, the color change is fully reversible and there's essentially no fatigue after many hot-cold cycles. The system or compound according to this invention changes color upon heating and turn back to the original color upon cooling. So at cold temperature the system or compound is in one chemical form and upon heating the system or compound changes color and is in another chemical form. In the instant case one form is a 6,11-dihydroxy-naphthacene-5,12-dione (e.g. a compound of formula (I) as defined below) and a base and the other form is a compound of formula (II). In a cool surrounding, the color is for example purple or blue which turns upon heating for example to orange or red. 6,11-Dihydroxy-naphthacene-5,12-diones are thermally quite stable so they can be extruded at high temperatures which is required for incorporation into common thermoplastic polymers.

The present invention pertains to a reversibly thermochromic system comprising a) a 6,11-dihydroxy-naphthacene-5,12-dione and b) a base.

Of interest is a reversibly thermochromic system, wherein component a is a compound of formula (I) or one of the tautomers thereof

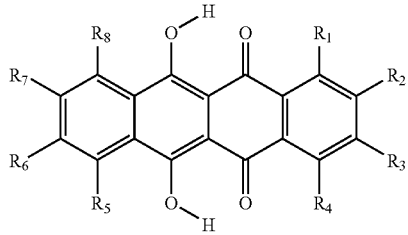

(I)

wherein
$R_1$, $R_2$, $R_3$, $R_4$, $R_5$, $R_6$, $R_7$ and $R_8$ independently are H, $C_1$-$C_{30}$alkyl, $C_7$-$C_{12}$aralkyl, $C_1$-$C_{30}$alkoxy, $C_1$-$C_{30}$alkylthio, $C_1$-$C_{30}$alkylsulfoxyl, $C_1$-$C_{30}$alkylsulfonyl, $C_2$-$C_{30}$alkenyl, $C_8$-$C_{12}$aralkenyl, $C_2$-$C_{30}$alkenyloxy, $C_2$-$C_{30}$alkenylthio, $C_2$-$C_{30}$alkenylsulfoxyl, $C_2$-$C_{30}$alkenylsulfonyl, $C_2$-$C_{30}$alkynyl, $C_8$-$C_{12}$aralkynyl, $C_2$-$C_{30}$alkynyloxy, $C_2$-$C_{30}$alkynylthio, $C_2$-$C_{30}$alkynylsulfoxyl, $C_2$-$C_{30}$alkynylsulfonyl, $C_6$-$C_{10}$aryl, $C_6$-$C_{10}$aryloxy, $C_6$-$C_{10}$arylthio, $C_6$-$C_{10}$arylsulfoxyl, $C_6$-$C_{10}$arylsulfonyl, halogen, $NO_2$, CN, COO—$R_9$, OCO—$R_{10}$, CO—$NR_9R_{11}$ or $NR_{12}$—CO—$R_{13}$, whereby the alkyl, alkenyl, alkynyl, aryl and aralkyl are substituted or unsubstituted,
or $R_2$, $R_3$, $R_6$ and/or $R_7$ are hydroxy;
or two adjacent groups of $R_1$, $R_2$, $R_3$, $R_4$, $R_5$, $R_6$, $R_7$ and $R_8$ form a 5- or 6-membered alicyclic or heterocyclic ring structure together with the two carbon atoms they are directly connected to;
or two of the substituents $R_1$, $R_2$, $R_3$, $R_4$, $R_5$, $R_6$, $R_7$ and $R_8$ are defined as follows:
one substituent is the group

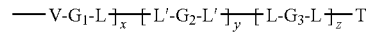

and the other substituent is the group so

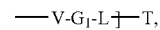

so the part of the one substituent with the open bracket and the part of the other substituent with the open bracket form together with the part of the molecule they are both attached to a monomer unit that is x times part in an oligomer or polymer;
$R_{10}$ and $R_{13}$ are independently $C_1$-$C_{30}$alkyl, $C_2$-$C_{30}$alkenyl, $C_2$-$C_{30}$alkynyl, $C_6$-$C_{10}$aryl, $C_7$-$C_{12}$aralkyl, $C_8$-$C_{12}$aralkenyl, $C_8$-$C_{12}$aralkynyl or an organic polymer, whereby the alkyl, alkenyl, alkynyl, aryl, aralkyl, aralkenyl and aralkynyl are substituted or unsubstituted;
$R_9$ is H or as defined for $R_{10}$;
$R_{11}$, and $R_{12}$ are independently H or $C_1$-$C_{30}$alkyl, $C_2$-$C_{30}$alkenyl, $C_2$-$C_{30}$alkynyl, $C_6$-$C_{10}$aryl, $C_7$-$C_{12}$aralkyl, $C_8$-$C_{12}$aralkenyl or $C_8$-$C_{12}$aralkynyl, whereby the alkyl, alkenyl, alkynyl, aryl aralkyl, aralkenyl and aralkynyl are substituted or unsubstituted;
V is independently $CH_2$, S, SO or $SO_2$;
$G_1$ is $C_1$-$C_{30}$alkylene;
L and L' are A or B; if L is A, then L' is B; if L is B, then L' is A;
A is O, S or $NR_{14}$;
$R_{14}$ is H, $C_1$-$C_{30}$alkyl, $C_2$-$C_{30}$alkenyl, $C_2$-$C_{30}$alkynyl, $C_6$-$C_{10}$aryl, $C_7$-$C_{12}$aralkyl, $C_8$-$C_{12}$aralkynyl or $C_8$-$C_{12}$aralkenyl;
B is CO;

$G_2$ is $C_1$-$C_{30}$alkylene; said alkylene is optionally interrupted by O, S, SO, $SO_2$, $NR_{14}$, or $G_2$ is one of the groups

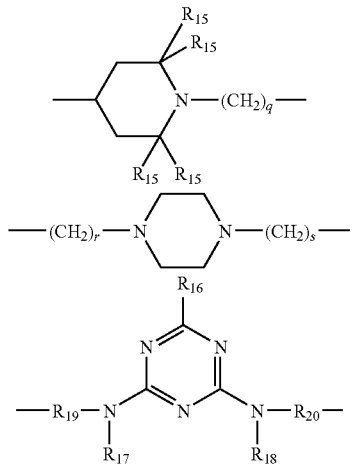

$R_{15}$ is H or $CH_3$;
q, r and s are independently integers from 1 to 20;
$R_{16}$ is $NH_2$, $NHR_{14}$, or

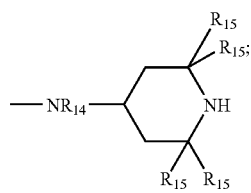

$R_{17}$ and $R_{18}$ are independently as defined for $R_{14}$ or

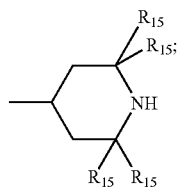

$R_{19}$ and $R_{20}$ are independently $C_1$-$C_{20}$alkylene;
$G_3$ has the same meanings as $G_2$;
T is H, if L is A; T is OH, if L=B;
x and y are independently integers from 1 to 20;
z is an integer from 0 to 20;
the substituted alkyl, alkenyl, alkynyl, aryl, aralkyl, aralkenyl and aralkynyl are substituted by halogen, hydroxy, nitro, cyano, COO—$R_{21}$, $CONR_{21}R_{22}$, OCO—$R_{23}$, $NR_{21}$CO—$R_{23}$, $NR_{21}R_{22}$, O—$R_{23}$, S—$R_{23}$, SO—$R_{23}$ and/or S(=O)$_2$—$R_{23}$; or the substituted aryl, aralkyl, aralkenyl and aralkynyl are substituted by $C_1$-$C_{30}$alkyl, $C_2$-$C_{30}$alkenyl and/or $C_2$-$C_{30}$alkynyl;
$R_{23}$ is $C_1$-$C_{30}$alkyl, $C_2$-$C_{30}$alkenyl, $C_2$-$C_{30}$alkynyl, $C_6$-$C_{10}$aryl, $C_7$-$C_{12}$aralkyl, $C_8$-$C_{12}$aralkenyl or $C_8$-$C_{12}$aralkynyl;
$R_{21}$ and $R_{22}$ are independently H or as defined for $R_{23}$.

Compounds of formula (I) may form tautomers of formula (101), (102) and/or (103).

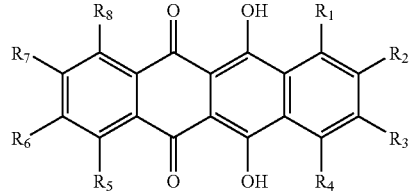

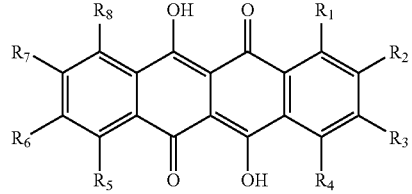

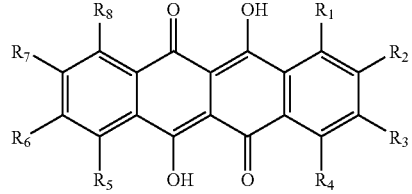

In oligomers or polymers of compound of formula (I) with one group

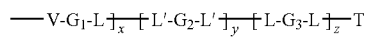

and one group

the units that are x, y and z times part of the molecule may be distributed randomly in the oligomer or in the polymer, with the proviso that no group L is directly connected to another group L and that no group L' is directly connected to another group L'.

Of interest are the substituent $R_1$, $R_4$, $R_5$ and $R_8$ not being COO—$CH_3$ and COO—$CH_2CH_3$, for example not being COO—$R_9$ with $R_9$=$C_1$-$C_4$alkyl, especially with $R_9$ being alkyl, in particular not being $COOR_9$. The alkyl mentioned in this paragraph is for example unsubstituted, in particular unsubstituted or substituted.

Of interest are substituents $R_2$, $R_3$, $R_6$ and $R_7$ not being COO-isobutyl and COO—$CH_2CH_2$—O—$C_2CH_3$, for example not being COO—$R_9$ with $R_9$ being substituted ethyl or unsubstituted butyl (e.g. branched, for instance branched or linear), in particular not being COO—$R_9$ with $R_9$ being unsubstituted or substituted $C_2$-$C_4$alkyl (e.g. unsubstituted or substituted $C_1$-$C_5$alkyl, in particular substituted or unsubstituted alkyl), especially not being COO—$R_9$.

Two adjacent groups of $R_1$, $R_2$, $R_3$, $R_4$, $R_5$, $R_6$, $R_7$ and $R_8$ is to be understood that the two adjacent groups are connected to two carbon atoms which are directly connected to each other.

For example, only one or two substituents $R_1$-$R_8$ contain groups $R_9$, $R_{10}$ or $R_{13}$ being an organic polymer, especially only one of the substituents $R_1$-$R_8$ contains said groups.

For instance, only $R_1$ and $R_4$ or $R_2$ and $R_3$ contain groups $R_9$, $R_{10}$ or $R_{13}$ being an organic polymer, e.g. only $R_2$ and $R_3$ contain said groups.

For example, only $R_1$ or $R_2$ contain a group $R_9$, $R_{10}$ or $R_{13}$ being an organic polymer, in particular only $R_2$ contains said group.

Of interest are organic polymers as $R_9$, $R_{10}$ or $R_{13}$ that are synthetic organic polymers.

Of further interest are organic polymers as $R_9$, $R_{10}$ or $R_{13}$ that contain at least one functional group such as OH, $NH_2$, NH, $CONH_2$, COO-alkyl (e.g. $C_1$-$C_{30}$alkyl, in particular methyl) and/or COOH prior to reaction and upon reaction form an ester or an amide group with the help of another appropriate functional group. Or also of further interest are organic polymers as $R_9$, $R_{10}$ or $R_{13}$ that contain acrylic units or vinyl groups, for example acrylic polymer or copolymer or polyolefins.

Examples of organic polymers as $R_9$, $R_{10}$ or $R_{13}$ are the polymers mentioned in the list below as items 1.-3., 5.-6a., 7., 9.-14., 18., 24. and 25.

In the definitions herein the term alkyl comprises within the limits of the carbon atoms given, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, 2-methylheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl and dodecyl.

For instance, the term alkyl comprises cycloalkyl such as cyclobutyl, cyclopentyl, cyclohexyl, methylcyclopentyl, dimethylcyclopentyl and methylcyclohexyl. Preferably, the term alkyl does not comprise cycloalkyl.

Examples of alkenyl are vinyl, allyl, butenyl, pentenyl, hexenyl, heptenyl, octenyl, nonenyl, decenyl, undecenyl and dodecenyl. The term alkenyl also comprises residues with more than one double bond that may be conjugated or non-conjugated.

Examples of alkynyl are ethynyl, 1-propynyl, 2-propynyl, butynyl, pentynyl, hexynyl, heptynyl, octynyl, nonynyl, decynyl, undecynyl and dodecynyl. The term alkynyl comprises residues with one or more triple bonds with optionally one or more double bonds whereby the unsaturated bonds may be conjugated or non-conjugated.

Examples of alkylene are methylene, ethylene, propylene, isopropylene, n-butylene, sec-butylene, isobutylene, tert-butylene, 2-ethylbutylene, n-pentylene, isopentylene, 1-methylpentylene, 1,3-dimethylbutylene, n-hexylene, 1-methylhexylene, n-heptylene, 2-methylheptylene, 1,1,3,3-tetramethylbutylene, 1-methylheptylene, 3-methylheptylene, n-octylene, 2-ethylhexylene, 1,1,3-trimethylhexylene, 1,1,3,3-tetramethylpentylene, nonylene, decylene, undecylene, 1-methylundecylene and dodecylene.

Examples of alkenylene are within the limits of the carbon atoms given vinylene, allylene, butenylene, pentenylene, hexenylene, heptenylene, octenylene, nonenylene, decenylene, undecenylene and dodecenylene. The term alkenylene also comprises residues with more than one double bond that may be conjugated or non-conjugated.

Aryl is for instance phenyl whereas aralkyl is for example benzyl.

An example of an aralkenyl is 2-phenylethenyl, an example of an aralkynyl is 2-phenylethynyl.

An example of arylene is phenylene.

For instance, alkoxy, alkylthio, alkylsulfoxyl or alkylsulfonyl means that an alkyl group as defined above with appropriate number of carbon atoms is connected to O, S, SO or $S(=O)_2$ respectively.

For example, alkenyloxy, alkenylthio, alkenylsulfoxyl or alkenylsulfonyl means that an alkenyl group as defined above with appropriate number of carbon atoms is connected to O, S, SO or $S(=O)_2$ respectively.

For example, alkynyloxy, alkynylthio, alkynylsulfoxyl or alkynylsulfonyl means that an alkynyl group as defined above with appropriate number of carbon atoms is connected to O, S, SO or $S(=O)_2$ respectively.

For instance, $C_6$-$C_{10}$aryloxy, $C_6$-$C_{10}$arylthio, $C_6$-$C_{10}$arylsulfoxyl or $C_6$-$C_{10}$arylsulfonyl means that an aryl group as defined above with appropriate number of carbon atoms is connected to O, S, SO or $S(=O)_2$ respectively.

Examples of halogen are F, Cl, Br and I, especially Cl and Br, in particular Cl.

Of particular interest is a reversibly thermochromic system, wherein $R_1$, $R_2$, $R_3$, $R_4$, $R_5$, $R_6$, $R_7$ and $R_8$ independently are H, $C_1$-$C_{30}$alkyl, $C_7$-$C_{12}$aralkyl, $C_1$-$C_{30}$alkoxy, $C_1$-$C_{30}$alkylthio, $C_1$-$C_{30}$alkylsulfoxyl, $C_1$-$C_{30}$alkylsulfonyl, $C_2$-$C_{30}$alkenyl, $C_8$-$C_{12}$aralkenyl, $C_2$-$C_{30}$alkenyloxy, $C_2$-$C_{30}$alkenylthio, $C_2$-$C_{30}$alkenylsulfoxyl, $C_2$-$C_{30}$alkenylsulfonyl, $C_2$-$C_{30}$alkynyl, $C_8$-$C_{12}$aralkynyl, $C_2$-$C_{30}$alkynyloxy, $C_2$-$C_{30}$alkynylthio, $C_2$-$C_{30}$alkynylsulfoxyl, $C_2$-$C_{30}$alkynylsulfonyl, $C_6$-$C_{10}$aryl, $C_6$-$C_{10}$aryloxy, $C_6$-$C_{10}$arylthio, $C_6$-$C_{10}$arylsulfoxyl, $C_6$-$C_{10}$arylsulfonyl, halogen, $NO_2$, CN, COO—$R_9$, OCO—$R_{10}$, CO—$NR_9R_{11}$ or $NR_{12}$—CO—$R_{13}$, whereby the alkyl, alkenyl, alkynyl, aryl and aralkyl are substituted or unsubstituted, or $R_2$, $R_3$, $R_6$ and/or $R_7$ are hydroxy;

or two adjacent groups of $R_1$, $R_2$, $R_3$, $R_4$, $R_5$, $R_6$, $R_7$ and $R_8$ form a 5- or 6-membered alicyclic or heterocyclic ring structure together with the two carbon atoms they are directly connected to, whereby the ring structure optionally contains one or two carbonyl groups and/or one or two hetero atoms, that are O, N, S, Se and/or P; the said ring structure is unsubstituted or substituted by $C_1$-$C_{30}$alkyl, $C_2$-$C_{30}$alkenyl, $C_2$-$C_{30}$alkynyl, unsubstituted or substituted $C_6$-$C_{10}$aryl, halogen, hydroxy, nitro, cyano, COO—$R_{21}$, $CONR_{21}R_{22}$, OCO—$R_{23}$, $NR_{21}$CO—$R_{23}$, $NR_{21}R_{22}$, O—$R_{23}$, S—$R_{23}$, SO—$R_{23}$, $S(=O)_2$—$R_{23}$, an organic poly- or oligomer, and/or an anellated 5- or 6-membered saturated or unsaturated ring structure that contain C and optionally one or two carbonyl groups and/or one or two hetero atoms, that are O, N, S, Se and/or P, the said anellated ring structure is unsubstituted or substituted by $C_1$-$C_{30}$alkyl, $C_2$-$C_{30}$alkenyl, $C_2$-$C_{30}$alkynyl, halogen, hydroxy, nitro, cyano, COO—$R_{21}$, $CONR_{21}R_{22}$, OCO—$R_{23}$, $NR_{21}$CO—$R_{23}$, $NR_{21}R_{22}$, O—$R_{23}$, S—$R_{23}$, SO—$R_{23}$, $S(=O)_2$—$R_{23}$, and/or anellated 5- or 6-membered saturated or unsaturated ring structure that contain C and optionally one or two carbonyl groups and/or one or two hetero atoms, that are O, N, S, Se and/or P;

or two of the substituents $R_1$, $R_2$, $R_3$, $R_4$, $R_5$, $R_6$, $R_7$ and $R_8$ are defined as follows:

one substituent is the group

and the other substituent is the group

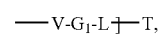

so the part of the one substituent with the open bracket and the part of the other substituent with the open bracket form together with the part of the molecule they are both attached to a monomer unit that is x times part in an oligomer or polymer;

q, r and s are independently integers from 1 to 5;

with the other substituents being as defined above.

Of special interest is a reversibly thermochromic system, wherein $R_1$, $R_2$, $R_3$, $R_4$, $R_5$, $R_6$, $R_7$ and $R_8$ independently are H, $C_1$-$C_{30}$alkyl, $C_7$-$C_{12}$aralkyl, $C_1$-$C_{30}$alkoxy, $C_1$-$C_{30}$alkylthio, $C_1$-$C_{30}$alkylsulfoxyl, $C_1$-$C_{30}$alkylsulfonyl, $C_2$-$C_{30}$alkenyl, $C_8$-$C_{12}$aralkenyl, $C_2$-$C_{30}$alkenyloxy, $C_2$-$C_{30}$alkenylthio, $C_2$-$C_{30}$alkenylsulfoxyl, $C_2$-$C_{30}$alkenylsulfonyl, $C_2$-$C_{30}$alkynyl, $C_8$-$C_{12}$aralkynyl, $C_2$-$C_{30}$alkynyloxy, $C_2$-$C_{30}$alkynylthio, $C_2$-$C_{30}$alkynylsulfoxyl, $C_2$-$C_{30}$alkynylsulfonyl, $C_6$-$C_{10}$aryl, $C_6$-$C_{10}$aryloxy, $C_6$-$C_{10}$arylthio, $C_6$-$C_{10}$arylsulfoxyl, $C_6$-$C_{10}$arylsulfonyl, halogen, $NO_2$, CN, COO—$R_9$, OCO—$R_{10}$, CO—$NR_9R_{11}$ or $NR_{12}$—CO—$R_{13}$, whereby the alkyl, alkenyl, alkynyl, aryl and aralkyl are substituted or unsubstituted, or $R_2$, $R_3$, $R_6$ and/or $R_7$ are hydroxy;

or $R_2$ and $R_3$ form a 5- or 6-membered alicyclic or heterocyclic ring structure together with the two carbon atoms they are directly connected to that is $R_2$ and $R_3$ form together the group CO—O—CO or CO—$NR_{24}$—CO;

or $R_2$ and $R_3$ are defined as follows:

one substituent is the group

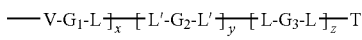

and the other substituent is the group

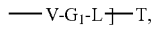

so the part of the one substituent with the open bracket and the part of the other substituent with the open bracket form together with the part of the molecule they are both attached to a monomer unit that is x times part in an oligomer or polymer;

$R_{24}$ is $C_2$-$C_{30}$alkyl, $C_2$-$C_{30}$alkenyl, $C_2$-$C_{30}$alkynyl, $C_6$-$C_{10}$aryl, $C_7$-$C_{12}$aralkyl, $C_8$-$C_{12}$aralkenyl, $C_8$-$C_{12}$aralkynyl or

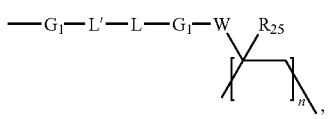

whereby the alkyl, alkenyl, alkynyl, aryl, aralkyl, aralkenyl and aralkynyl are substituted or unsubstituted as defined above;

q is an integer from 2 to 4;

r and s are independently integers from 1 to 3;

W is $C_6$-$C_{10}$arylene, $C_1$-$C_{30}$alkylene, $C_1$-$C_{30}$alk-1-enylene, $NR_{11}$ or O;

$R_{25}$ is H or $C_1$-$C_4$alkyl;

with the other substituents being as above.

Of further particular interest is reversibly thermochromic system, wherein $R_1$, $R_2$, $R_3$, $R_4$, $R_5$, $R_6$, $R_7$ and $R_8$ independently are H, $C_1$-$C_{30}$alkyl, $C_7$-$C_{12}$aralkyl, $C_1$-$C_{30}$alkoxy, $C_1$-$C_{30}$alkylthio, $C_1$-$C_{30}$alkylsulfoxyl, $C_1$-$C_{30}$alkylsulfonyl, $C_6$aryl, $C_6$arylthio, $C_6$arylsulfoxyl, $C_6$arylsulfonyl, halogen, COO—$R_9$, OCO—$R_{10}$, whereby the alkyl and aryl are substituted or unsubstituted, or $R_2$ and $R_3$ form a 5- or 6-membered alicyclic or heterocyclic ring structure together with the two carbon atoms they are directly connected to that is $R_2$ and $R_3$ form together the group CO—O—CO or CO—$NR_{24}$—CO;

or $R_2$ and $R_3$ are defined as follows:

one substituent is the group

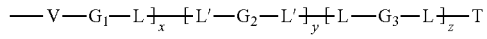

and the other substituent is the group

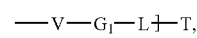

so the part of the one substituent with the open bracket and the part of the other substituent with the open bracket form together with the part of the molecule they are both attached to a monomer unit that is x times part in an oligomer or polymer;

$R_{10}$ is $C_1$-$C_{30}$alkyl or $C_6$aryl, whereby the alkyl and aryl is substituted or unsubstituted;

$R_9$ is H or as defined for $R_{10}$;

$R_{24}$ is unsubstituted or substituted $C_2$-$C_{30}$alkyl or $C_6$aryl;

V is $SO_2$;

$G_1$ is $C_2$-$C_{10}$alkylene;

L and L' are A or B; if L is A, then L' is B; if L is B, then L' is A;

A is O;

B is CO;

$G_2$ is $C_2$-$C_{10}$alkylene;

$G_3$ has the same meanings as $G_2$;

T is H, if L is A; T is OH, if L=B;

x and y are independently integers from 1 to 10;

z is an integer from 0 to 10;

the substituted alkyl and substituted aryl are substituted by hydroxy, COO—$R_{21}$, OCO—$R_{23}$ and/or O—$R_{23}$; or the aryl is substituted by $C_1$-$C_{15}$alkyl;

$R_{23}$ is $C_1$-$C_{15}$-alkyl;

$R_{21}$ is H or as defined for $R_{23}$.

Of further special interest is a reversibly thermochromic system, wherein $R_1$, $R_2$, $R_3$, $R_4$, $R_5$, $R_6$, $R_7$ and $R_8$ independently are H, $C_1$-$C_{30}$alkylthio, $C_1$-$C_{30}$alkylsulfonyl, COO—$R_9$, $C_6$aryl, whereby the alkyl is substituted or unsubstituted, or $R_2$ and $R_3$ form a 5- or 6-membered alicyclic or heterocyclic ring structure together with the two carbon atoms they are directly connected to that is $R_2$ and $R_3$ form together the group CO—O—CO or CO—$NR_{24}$—CO;

or $R_2$ and $R_3$ are defined as follows:

one substituent is the group

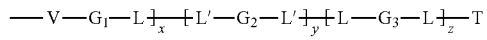

and the other substituent is the group

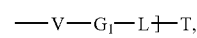

so the part of the one substituent with the open bracket and the part of the other substituent with the open bracket form together with the part of the molecule they are both attached to a monomer unit that is x times part in an oligomer or polymer;
$R_9$ is H or $C_1$-$C_{30}$alkyl, whereby the alkyl is substituted or unsubstituted;
$R_{24}$ is unsubstituted or substituted $C_2$-$C_{30}$alkyl or $C_6$aryl;
V is $SO_2$;
$G_1$ is $C_2$-$C_{10}$alkylene;
L and L' are A or B; if L is A, then L' is B; if L is B, then L' is A;
A is O;
B is CO;
$G_2$ is $C_2$-$C_{10}$alkylene;
$G_3$ has the same meanings as $G_2$;
T is H, if L is A; T is OH, if L=B;
x and y are independently integers from 1 to 10;
z is an integer from 0 to 10;
the substituted alkyl and substituted aryl are substituted by hydroxy and/or COO—$R_{21}$; or the aryl is substituted by $C_1$-$C_{15}$alkyl;
$R_{21}$ is H or $C_1$-$C_{15}$alkyl.

Of most particular interest is a reversibly thermochromic system, wherein
$R_1$, $R_2$, $R_3$, $R_4$, $R_5$, $R_6$, $R_7$ and $R_8$ independently are H, $C_2$-$C_{20}$alkylthio, $C_2$-$C_{20}$alkylsulfonyl, COO—$R_9$, $C_6$aryl, whereby the alkyl is substituted or unsubstituted,
or $R_2$ and $R_3$ form a 5- or 6-membered alicyclic or heterocyclic ring structure together with the two carbon atoms they are directly connected to that is $R_2$ and $R_3$ form together the group CO—O—CO or CO—$NR_{24}$—CO;
$R_9$ is H or $C_3$-$C_{20}$alkyl, whereby the alkyl is substituted or unsubstituted;
$R_{24}$ is unsubstituted or substituted $C_4$-$C_{20}$alkyl or $C_6$aryl;
the substituted alkyl and substituted aryl are substituted by hydroxy and/or COO—$R_{21}$; or the aryl is substituted by $C_1$-$C_{15}$alkyl;
$R_{21}$ is H or $C_1$-$C_{15}$alkyl.

An example is a reversibly thermochromic system, wherein one to four substituents $R_1$-$R_8$ are not H.

Another example is a reversibly thermochromic system, wherein $R_1$, $R_4$, $R_5$ and $R_8$ are H and $R_2$, $R_3$, $R_6$ and $R_7$ are not H.

A further example is a reversibly thermochromic system, wherein $R_1$ and $R_4$-$R_8$ are H and $R_2$ and $R_3$ are not H.

Another example is a reversibly thermochromic system, wherein $R_1$ and $R_3$-$R_8$ are H and $R_2$ is not H.

Of utmost interest is a reversibly thermochromic system, wherein
at least one of $R_1$, $R_2$, $R_3$, $R_4$, $R_5$, $R_6$, $R_7$ and $R_8$ is or contains a sulfoxyl, a sulphonyl, an ester, an ether or an amide group, whereby if the sulphonyl group is phenylsulphonyl, at least two of $R_1$, $R_2$, $R_3$, $R_4$, $R_5$, $R_6$, $R_7$ and $R_8$ are phenylsulphonyl, or two groups of $R_1$, $R_2$, $R_3$, $R_4$, $R_5$, $R_6$, $R_7$ and $R_8$ are carboxy, or two adjacent groups of $R_1$, $R_2$, $R_3$, $R_4$, $R_5$, $R_6$, $R_7$ and $R_8$ form a 5- or 6-membered cyclic ring structure that is not maleic acid methyl imide or benzene or the compound of formula (I) is an oligomer or a polymer.

These sulfoxyl, sulphonyl, ester, ether and amide groups and 5- or 6-membered cyclic ring structure are the ones defined above.

Maleic acid methyl imide and benzene means that said residues are formed by two adjacent groups of $R_1$, $R_2$, $R_3$, $R_4$, $R_5$, $R_6$, $R_7$ and $R_8$ together with the two carbon atoms the two adjacent groups are directly connected to.

The compound of formula (I) is an oligomer or a polymer means that it is part of an oligomer or polymer. For example, this means that at least one of the substituents $R_1$-$R_8$ contain a group $R_9$, $R_{10}$ and/or $R_{13}$ being an organic polymer or that two of the substituents $R_1$, $R_2$, $R_3$, $R_4$, $R_5$, $R_6$, $R_7$ and $R_8$ are defined as follows:
one substituent is the group

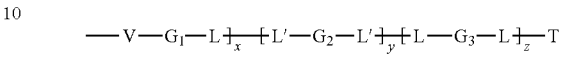

and the other substituent is the group

Preference is given to a reversibly thermochromic system, wherein the base b has a molecular weight of at least 150.

Particular preference is given to a reversibly thermochromic system, wherein the base b has a molecular weight of at least 300.

For instance, the molecular weight is expressed in grams per mole.

More particular preference is given to a reversibly thermochromic system, wherein the base b is an secondary or tertiary amine or a secondary or tertiary phosphine, whereby said amine and said phosphine are not aromatic and do not have aromatic substituents that are directly connected to said amine or said phosphine.

The secondary or tertiary amine or the secondary or tertiary phosphine has two or three organic substituents.

For example, the secondary amine is $NHR_{26}R_{27}$, the tertiary amine is $NR_{26}R_{27}R_{28}$, the secondary phosphine is $PHR_{26}R_{27}$ and the tertiary phosphine is $PR_{26}R_{27}R_{28}$, wherein $R_{26}$, $R_{27}$ and $R_{28}$ are independently an organic residue containing 1-500 carbon atoms and optionally 1-200 heteroatoms, in particular N, P, O, S, Se, Cl, Br and/or I; or $R_{26}$ and $R_{27}$ form together with the N they are connected to an optionally substituted 5- or 6-membered cyclic ring structure; for instance, such an optionally substituted cyclic ring structure is a sterically hindered amine;
with the proviso that the secondary or tertiary amine or the secondary or tertiary phosphine does not contain acidic groups such as COOH and $SO_2OH$.

For instance, $R_{26}$, $R_{27}$ and $R_{28}$ are independently $C_1$-$C_{30}$alkyl, $C_7$-$C_{12}$aralkyl, $C_2$-$C_{30}$alkenyl, $C_8$-$C_{12}$aralkenyl, $C_2$-$C_{30}$alkynyl or $C_8$-$C_{12}$aralkynyl, the said groups are unsubstituted or substituted by one or more COO—$R_{21}$, $CONR_{21}R_{22}$, OCO—$R_{23}$, $NR_{21}CO$—$R_{23}$, $NR_{23}R_{21}$, O—$R_{23}$, S—$R_{23}$, SO—$R_{23}$ and/or $S(=O)_2$—$R_{23}$; or the aralkyl, aralkenyl and aralkynyl are substituted by $C_1$-$C_{30}$alkyl, $C_2$-$C_{30}$alkenyl and/or $C_2$-$C_{30}$alkynyl; or the said amine is a sterically hindered amine; $R_{21}$, $R_{22}$ and $R_{23}$ are as defined above.

Most particular preference is given to a reversibly thermochromic system, wherein the base b is a secondary or tertiary amine, for instance a secondary amine, for example a secondary or tertiary sterically hindered amine such as a secondary sterically hindered amine.

The secondary or tertiary sterically hindered amine is preferably a compound of formula (III)

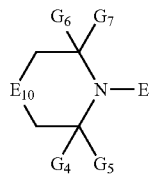
(III)

wherein $G_4$, $G_5$, $G_6$ and $G_7$ are independently methyl or ethyl, for example methyl;

E is hydrogen, $C_1$-$C_{18}$alkyl or $C_3$-$C_{18}$alkenyl, for example $C_1$-$C_{18}$alkyl or hydrogen, in particular hydrogen;

$E_{10}$ is a carbon atom which is unsubstituted or substituted by OH, =O or by one or two organic residues containing in total 1-500 carbon atoms.

The secondary or tertiary sterically hindered amine is preferably one of formulae (A) to (M)

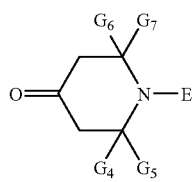
(A)

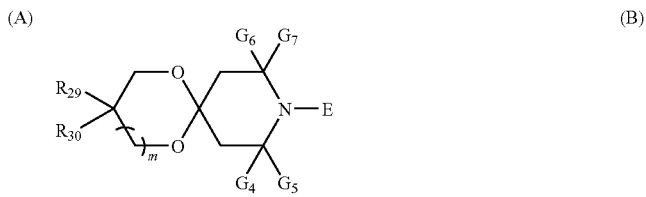
(B)

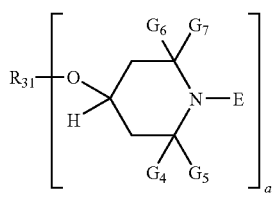
(C)

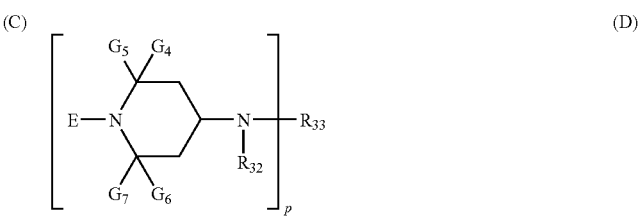
(D)

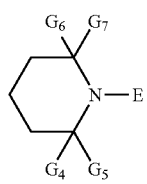
(E)

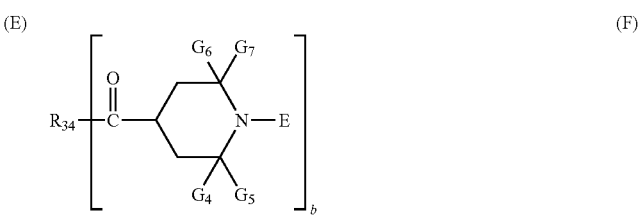
(F)

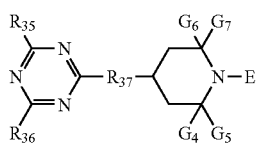
(G)

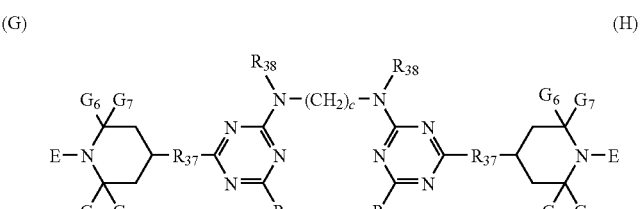
(H)

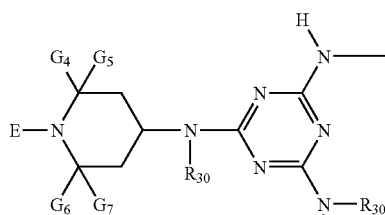
(I)

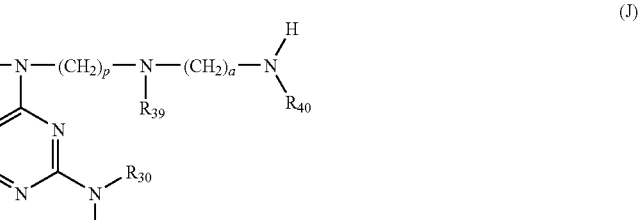
(J)

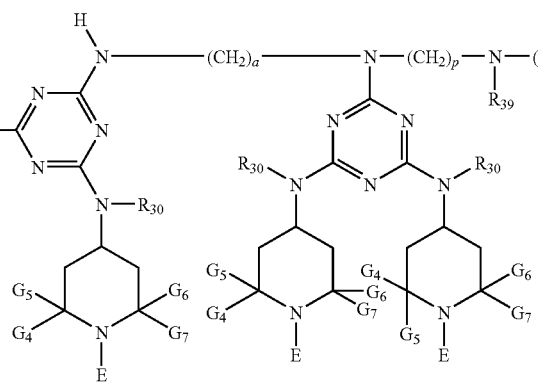

(K)

[structure showing R_38, (CH2CH2)_m, H, R_37, O, G_5, G_4, N-E, G_6, G_7, subscript d]

[structure showing R_44-O, R_44-O, G_6, G_7, N-E, G_5, G_4]

-continued (L)

[structure showing R_42—N—(CH2)_c—N— piperidine rings with G_4, G_5, G_6, G_7, N-E, triazine with N, N, N, R_41, R_43, subscript e]

(M)

wherein E, $G_4$, $G_5$, $G_6$ and $G_7$ are as defined above;

m is 0 or 1;

$R_{29}$ is hydrogen, hydroxyl or hydroxymethyl;

$R_{30}$ is hydrogen, alkyl of 1 to 12 carbon atoms or alkenyl of 2 to 12 carbon atoms;

a is 1 to 4;

when a is 1, $R_{31}$ is hydrogen, alkyl of 1 to 18 carbon atoms, alkoxycarbonylalkylenecarbonyl of 4 to 18 carbon atoms, alkenyl of 2 to 18 carbon atoms, glycidyl, 2,3-dihydroxypropyl, 2-hydroxy or 2-(hydroxymethyl) substituted alkyl of 3 to 12 carbon atoms which alkyl is interrupted by oxygen, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, or acyl radical of an aromatic acid containing 7 to 15 carbon atoms;

when a is 2, $R_{31}$ is alkylene of 2 to 18 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

when a is 3, $R_{31}$ is a trivalent acyl radical of an aliphatic or unsaturated aliphatic tricarboxylic acid containing 6 to 18 carbon atoms, or a trivalent acyl radical of an aromatic tricarboxylic acid containing 9 to 15 carbon atoms;

when a is 4, $R_{31}$ is a tetravalent acyl radical of an aliphatic or unsaturated aliphatic tetracarboxylic acid, especially 1,2,3,4-butanetetracarboxylic acid, 1,2,3,4-but-2-enetetracarboxylic acid, 1,2,3,5-pentanetetracarboxylic acid and 1,2,4,5-pentanetetracarboxylic acid, or $R_{31}$ is a tetravalent acyl radical of an aromatic tetracarboxylic acid containing 10 to 18 carbon atoms;

p is 1 to 3, $R_{32}$ is hydrogen, alkyl of 1 to 18 carbon atoms or acyl of 2 to 6 carbon atoms or phenyl;

when p is 1, $R_{33}$ is phenyl, alkyl of 1 to 18 carbon atoms, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, an acyl radical of an aromatic carboxylic acid containing 7 to 15 carbon atoms, or $R_{32}$ and $R_{33}$ together are —$(CH_2)_5CO$—, phthaloyl or a divalent acyl radical of maleic acid;

when p is 2, $R_{33}$ is alkylene of 2 to 12 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

when p is 3, $R_{33}$ is a trivalent acyl radical of an aliphatic or unsaturated aliphatic tricarboxylic acid containing 6 to 18 carbon atoms, or a trivalent acyl radical of an aromatic tricarboxylic acid containing 9 to 15 carbon atoms;

b is 1 to 4, when b is 1, $R_{34}$ is alkoxy of 1 to 18 carbon atoms, alkenyloxy of 2 to 18 carbon atoms, —NHalkyl of 1 to 18 carbon atoms or —N(alkyl)$_2$ of 2 to 36 carbon atoms, when b is 2, $R_{34}$ is alkylenedioxy of 2 to 18 carbon atoms, alkenylenedioxy of 2 to 18 carbon atoms, —NH-alkylene-NH— of 2 to 18 carbon atoms or —N(alkyl)-alkylene-N(alkyl)- of 2 to 18 carbon atoms, or $R_{34}$ is 4-methyl-1,3-phenylenediamino, when b is 3, $R_{34}$ is a trivalent alkoxy radical of a saturated or unsaturated aliphatic triol containing 3 to 18 carbon atoms, when b is 4, $R_{34}$ is a tetravalent alkoxy radical of a saturated or unsaturated aliphatic tetraol containing 4 to 18 carbon atoms, $R_{35}$ and $R_{36}$ are independently chlorine, alkoxy of 1 to 18 carbon atoms, —O-$T_1$, amino substituted by 2-hydroxyethyl, —NH(alkyl) of 1 to 18 carbon atoms, —N(alkyl)$T_1$ with alkyl of 1 to 18 carbon atoms, or —N(alkyl)$_2$ of 2 to 36 carbon atoms, $R_{37}$ is oxygen, or $R_{37}$ is nitrogen substituted by either hydrogen, alkyl of 1 to 12 carbon atoms or $T_1$, $T_1$ is

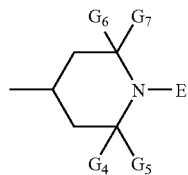

$R_{38}$ is hydrogen or methyl,
c is 2 to 8,
$R_{39}$ and $R_{40}$ are independently hydrogen or the group $T_2$,
$T_2$ is

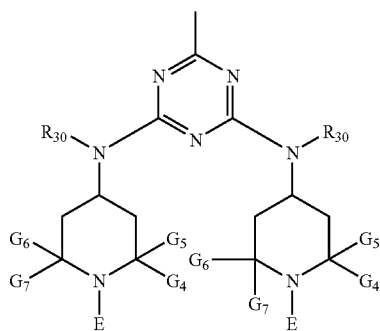

e is 1 to 10, for example 2-10;
d is an integer such that the compound has a molecular weight of 1000 to 4000 amu, e.g. d may be from the range 3-10;
$R_{41}$ is morpholino, piperidino, 1-piperizinyl, alkylamino of 1 to 10 carbon atoms, especially branched alkylamino of 3 to 8 carbon atoms such as tert-octylamino, —N(alkyl)$T_1$ with alkyl of 1 to 8 carbon atoms, or —N(alkyl)$_2$ of 2 to 16 carbon atoms,
$R_{42}$ is hydrogen, acyl of 2 to 4 carbon atoms, carbamoyl substituted by alkyl of 1 to 4 carbon atoms, s-triazinyl substituted once by chlorine and once by $R_{41}$, or s-triazinyl substituted twice by $R_{41}$ with the condition that the two $R_{41}$ substituents may be different;
$R_{43}$ is chlorine, amino substituted by alkyl of 1 to 8 carbon atoms or by $T_1$, —N(alkyl)$T_1$ with alkyl of 1 to 8 carbon atoms, —N(alkyl)$_2$ of 2 to 16 carbon atoms, or the group $T_3$,
$T_3$ is

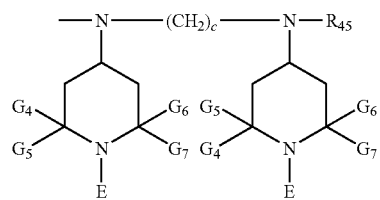

$R_{45}$ is hydrogen, acyl of 2 to 4 carbon atoms, carbamoyl substituted by alkyl of 1 to 4 carbon atoms, s-triazinyl substituted twice by —N(alkyl)$_2$ of 2 to 16 carbon atoms or s-triazinyl substituted twice by —N(alkyl)$T_1$ with alkyl of 1 to 8 carbon atoms;
$R_{44}$ is independently hydrogen, alkyl of 1 to 18 carbon atoms, alkoxycarbonylalkylene-carbonyl of 4 to 18 carbon atoms, alkenyl of 2 to 18 carbon atoms, glycidyl, 2,3-dihydroxypropyl, 2-hydroxy or 2-(hydroxymethyl) substituted alkyl of 3 to 12 carbon atoms which alkyl is interrupted by oxygen, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, or acyl radical of an aromatic acid containing 7 to 15 carbon atoms.

The secondary or tertiary sterically hindered amine is more preferably of formula (D) or (L), in particular of formula (L).

For instance, the secondary or tertiary sterically hindered amine is of formula (C).

In formula (C), preference is given to the following:
a is 1 or 2, preferably 2;
when a is 1,
$R_{31}$ is hydrogen, alkyl of 1 to 18 carbon atoms or an acyl radical of an aliphatic or unsaturated aliphatic carboxylic or carbamic acid containing 2 to 18 carbon atoms, preferably $R_{31}$ is alkyl of 1 to 18 carbon atoms or an acyl radical of an aliphatic carboxylic acid containing 2 to 18 carbon atoms, most preferably $R_{31}$ is an acyl radical of an aliphatic carboxylic acid containing 2 to 18 carbon atoms;
when a is 2,
$R_{31}$ is alkylene of 2 to 18 carbon atoms or a divalent acyl radical of an aliphatic or unsaturated aliphatic dicarboxylic or dicarbamic acid containing 2 to 18 carbon atoms, preferably $R_{31}$ is alkylene of 2 to 18 carbon atoms or a divalent acyl radical of an aliphatic dicarboxylic acid containing 2 to 18 carbon atoms, most preferably $R_{31}$ is a divalent acyl radical of an aliphatic dicarboxylic acid containing 2 to 18 carbon atoms;

In formula (D), preference is given to the following:
p is 1 or 2, preferably 2;
$R_{32}$ is hydrogen or alkyl of 1 to 18 carbon atoms, preferably hydrogen;
when p is 1,
$R_{33}$ is alkyl of 1 to 18 carbon atoms or an acyl radical of an aliphatic or unsaturated aliphatic carboxylic or carbamic acid containing 2 to 18 carbon atoms, for example $R_{33}$ is alkyl or an acyl radical of an aliphatic carboxylic acid containing 2 to 18 carbon atoms;
when p is 2,
$R_{33}$ is alkylene of 2 to 12 carbon atoms or a divalent acyl radical of an aliphatic or unsaturated aliphatic dicarboxylic or dicarbamic acid containing 2 to 18 carbon atoms, for instance $R_{33}$ is alkylene of 2 to 12 carbon atoms.

In formula (L), preference is given to the following:
c is 4 to 8;
$R_{41}$ is alkylamino of 1 to 10 carbon atoms, especially branched alkylamino of 3 to 8 carbon atoms such as tert-octylamino, —N(alkyl)$T_1$ with alkyl of 1 to 8 carbon atoms, or —N(alkyl)$_2$ of 2 to 16 carbon atoms;
$R_{42}$ is hydrogen, s-triazinyl substituted once by chlorine and once by $R_{41}$ or s-triazinyl substituted twice by $R_{41}$ with the condition that the two $R_{41}$ substituents may be different, for example $R_{42}$ is hydrogen or s-triazinyl substituted twice by $R_{41}$;
$R_{43}$ is as described above, for example $R_{43}$ is the group $T_3$,
$R_{45}$ of the group $T_3$ is hydrogen, s-triazinyl substituted twice by —N(alkyl)$_2$ of 2 to 16 carbon atoms or s-triazinyl substituted twice by —N(alkyl)$T_1$ with alkyl of 1 to 8 carbon atoms, for example $R_{45}$ of the group $T_3$ is hydrogen or s-triazinyl substituted twice by —N(alkyl)$_2$ of 2 to 16 carbon atoms.

The following commercially available products are suitable as sterically hindered amines: TINUVIN® 622 (CAS 65447-77-0), HOSTAVIN® N 30 (CAS 202483-55-4), FERRO® AM 806 (CAS 70800-09-8), DASTIB® 845 (CAS 24860-22-8), TINUVIN® 770 (CAS 58829-07-9), TINU- VIN® 765 (CAS 82919-37-7 and 41556-26-7), TINUVIN® 144 (CAS 63843-89-0), ADK STAB® LA 52 (CAS 91788-83-9), ADK STAB® LA 57 (CAS 64022-61-3), ADK STAB® LA 62 (CAS 107119-91-5), ADK STAB® LA 67 (CAS 100631-43-4), HOSTAVIN® N 20 (CAS 64338-16-5), HOSTAVIN® N 24 (CAS 85099-51-0 and 85099-50-9), SANDUVOR® 3050 (CAS 85099-51-0 and 85099-50-9), DIACETAM® 5 (CAS 76505-58-3), SUMISORB® TM 61 (CAS 84214-94-2), UVINUL® 4049 (CAS 109423-00-9), SANDUVOR® PR 31 (CAS 147783-69-5), GOODRITE® UV 3034 (CAS 71029-16-8), GOODRITE® UV 3150 (CAS 96204-36-3), GOODRITE® UV 3159 (CAS 130277-45-1), GOODRITE® 3110×128, UVINUL® 4050H (CAS 124172-53-8), CHIMASSORB® 944 (CAS 71878-19-8), CHIMASSORB® 2020 (CAS 192268-64-7), CYASORB® UV 3346 (CAS 82451-48-7), CYASORB® UV 3529 (CAS 193098-40-7), DASTIB® 1082 (CAS 113169-96-3), CHIMASSORB® 119 (CAS 106990-43-6), UVASIL® 299 (CAS 164648-93-5), UVASIL® 125 (CAS 164648-93-5), UVASIL® 2000 (CAS 164648-93-5), UVINUL® 5050H(CAS 152261-33-1 and 199237-39-3), LICHTSCHUTZSTOFF® UV 31, LUCHEM® HA B 18, ADK STAB® LA 63 (CAS 115055-30-6), ADK STAB® LA 68 (CAS 100631-44-5) or UVASORB® HA 88 (CAS 136504-96-6).

GOODRITE® 3110×128 is of formula

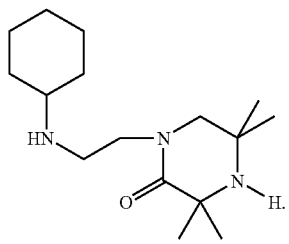

Lichtschutzstoff® UV 31 is of formula

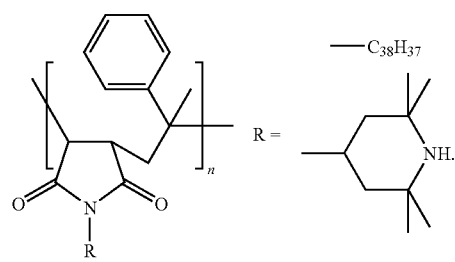

Of interest is a commercially available secondary sterically hindered amine that is Chimassorb® 944 (CAS 71878-19-8) or Chimassorb® 2020 (CAS 192268-64-7) or Tinuvin® 770 (CAS 58829-07-9), especially Chimassorb® 944 or Chimassorb® 2020.

Some examples of an aliphatic carboxylic acid are acetic, propionic, butyric, stearic acid. An example of a cycloaliphatic carboxylic acid is cyclohexanoic acid. An example of an aromatic carboxylic acid is benzoic acid. An example of an aliphatic dicarboxylic acid is malonyl, maleoyl, succinyl, adipic or sebacic acid. An example of a residue of an aromatic dicarboxylic acid is phthaloyl.

Acyl radicals of monocarboxylic acids are, within the definitions, a residue of the formula —CO—R'', wherein R'' may stand inter alia for an alkyl, alkenyl, cycloalkyl or aryl radical as defined. Preferred acyl radicals include acetyl, benzoyl, acryloyl, methacryloyl, propionyl, butyryl, valeroyl, hexanoyl, heptanoyl, octanoyl, nonanoyl, decanoyl, undecanoyl, dodecanoyl, pentadecanoyl, stearoyl. Polyacyl radicals of polyvalent acids are of the formula $(—CO)_{n1}—R''$, wherein n1 is the valency, e.g. 2, 3, 4, 5 or 6.

The ratio of component a to component b is preferably 2:1 to 1:100 by weight, more preferably 1:1 to 1:20 by weight, most preferably 1:2 to 1:16 by weight, for example 1:3 to 1:6 by weight.

This invention also relates to a compound of formula (II) or one of its tautomers

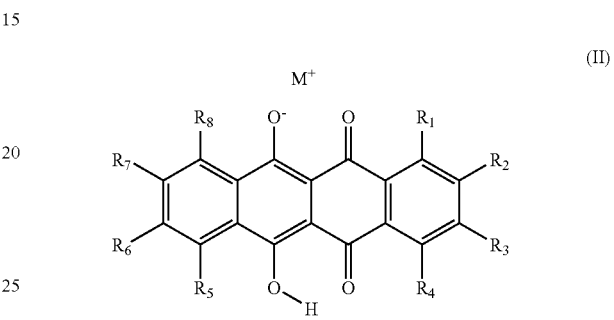

wherein $R_1$-$R_8$ are as defined above;

$M^+$ is an ammonium cation or a phosphonium cation with the proviso that the ammonium cation and the phosphonium cation are not aromatic and do not have aromatic substituents which are directly connected to said ammonium cation or said phosphonium cation.

The compound of formula (II) may form tautomers. For example, these tautomers are compounds of formulae (104)-(110)

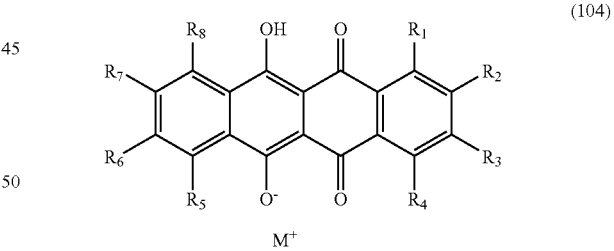

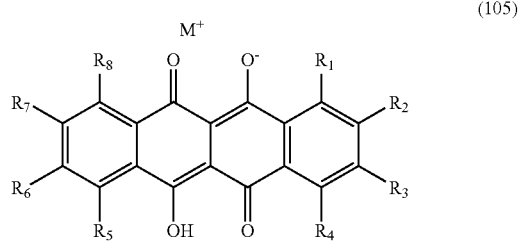

-continued

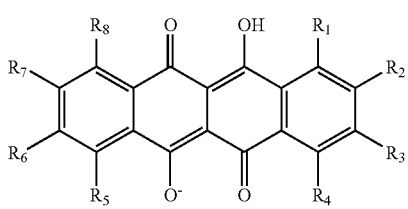
(106)

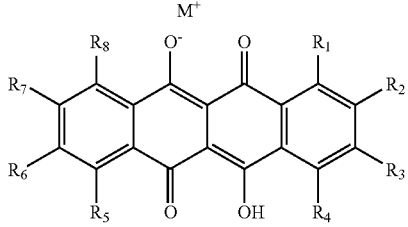
(107)

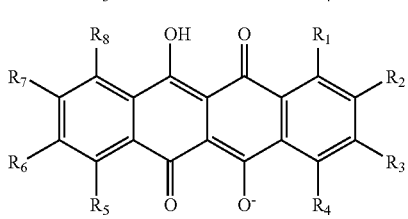
(108)

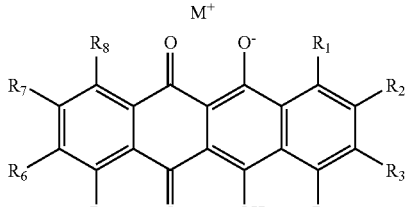
(109)

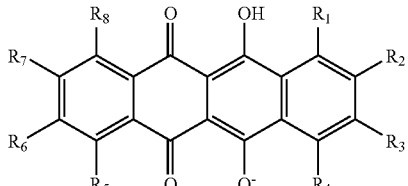
(110)

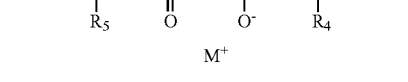

Preference is given to such compounds of formula (II), wherein $R_1$-$R_8$ are not chloro, e.g. not halogen.

For example, $M^+$ is a secondary or tertiary ammonium cation or a secondary or tertiary phosphonium cation.

Preferably, $M^+$ has a molecular weight of at least 150, more preferably of at least 300, most preferably of at least 350.

Preference is given to $M^+$ being a secondary or tertiary ammonium cation, for example a secondary ammonium cation, in particular a secondary or tertiary sterically hindered ammonium cation, e.g. a secondary sterically hindered ammonium cation.

For instance, these secondary or tertiary ammonium cation or a secondary or tertiary phosphonium cation or a secondary or tertiary sterically hindered ammonium cation correspond to the secondary or tertiary amine or the secondary or tertiary phosphine or the secondary or tertiary sterically hindered amine as defined above that carry an additional $H^+$ at the amine or phosphine functional group.

Another embodiment of this invention is a reversibly thermochromic composition, comprising
i) a reversibly thermochromic system as above or a compound of formula (II) as above and
ii) a carrier material.

The ratio of component i to component ii is preferably 1:10000 to 1:1, more preferably 1:5000 to 1:2, most preferably 1:1000 to 1:5.

For example, the carrier material ii is polymers, solvents and/or waxes.

For instance, the carrier material ii is plastic articles, films, papers, fibers, solvents, waxes, coatings and/or inks.

Example of polymers suitable as carrier material ii are
1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
  a) radical polymerisation (normally under high pressure and at elevated temperature).
  b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LL-DPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is gene-rated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

29. Blends of the aforementioned polymers (polyblends), for example PP/EPDM, Poly-amide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Incorporation into the organic polymers can be effected, for example, by mixing in or applying to a 6,11-dihydroxy-naphthacene-5,12-dione and a base or by mixing in or applying to a compound of formula (II) and, if desired, further additives by the methods which are customary in the art. The incorporation can take place prior to or during the shaping operation, or by applying the dissolved or dispersed compound to the polymer, with or without subsequent evaporation of the solvent. In the case of elastomers, these can also be stabilized as lattices. A further possibility for incorporating the compounds mentioned above into polymers is to add them before, during or directly after the polymerization of the corresponding monomers or prior to crosslinking. In this context the compounds mentioned above can be added as it is or else in encapsulated form (for example in waxes, oils or polymers).

The compounds mentioned herein can also be added in the form of a masterbatch containing said compound in a concentration, for example, of from 2.5 to 25% by weight to the carrier material ii.

The compounds mentioned herein can judiciously be incorporated by the following methods:
as emulsion or dispersion (e.g. to lattices or emulsion polymers),
as a dry mixture during the mixing in of additional components or polymer mixtures,
by direct introduction into the processing apparatus (e.g. extruders, internal mixers, etc),
as solution or melt.

A 6,11-dihydroxy-naphthacene-5,12-dione and a base, or a compound of formula (II), with or without further additives, can also be sprayed onto the carrier material ii such as plastic article, fiber, film, paper or coating. It is able to dilute other additives (for example the conventional additives indicated above) or their melts so that they too can be sprayed together with these additives onto the carrier material ii.

Of interest is a reversibly thermochromic composition as defined above, comprising further additives.

Preferably, the further additives are
antioxidants, UV-absorbers, light stabilizers, metal deactivators, processing stabilizers, thiosynergists, peroxide scavengers, oxygen scavengers, basic co-stabilizers, nucleating agents, fillers, reinforcing agents, flameproofing agents and/or additional colorants with the proviso that the additional colorants do not suppress and do not mask the thermochromic effect.

Most preferably, the further additives are
phenolic antioxidants, aminic antioxidants, phosphites, phosphonites, hydroxylamines, nitrones, benzofuranones, indolinones, 2-(2-hydroxyphenyl)benzotriazoles, 2-hydroxybenzophenones, 2-(2-hydroxyphenyl)-1,3,5-triazines, oxamides, sterically hindered amines, pigments and/or dyes.

Examples of such further additives are

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctyl-thiomethyl-6-methylphenol, 2,4-dioctylthiomethyl-6-ethyl phenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octade-cyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2, 2'-thiobis(6-tert-butyl-4-methylphenol), 2,2'-thiobis(4-octyl phenol), 4,4'-thiobis(6-tert-butyl-3-methyl phenol), 4,4'-thiobis(6-tert-butyl-2-methyl phenol), 4,4'-thiobis(3,6-di-sec-amylphenol), 4,4'-bis(2,6-dimethyl-4-hydroxyphenyl)-disulfide.

1.6. Alkylidenebisphenols, for example 2, 2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis [6-(α-methyl benzyl)-4-nonylphenol], 2,2'-methylenebis[6-(α,α-dimethyl benzyl)-4-nonylphenol], 4,4'-methylenebis(2, 6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopenta-diene, bis[2-(3'-tert-butyl-2'-hydroxy-5'-methyl-benzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1, 5,5-tetra-(5-tert-butyl-4-hydroxy-2-methylphenyl)pentane.

1.7. O-, N- and S-benzyl compounds, for example 3, 5,3', 5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxy-benzyl)-2,4,6-trimethylbenzene, 1,4-bis(3,5-di-tert-butyl-4-hydroxybenzyl)-2, 3,5,6-tetramethyl benzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-tri-azine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4, 6-tris-(3,5-di-tert-butyl-4-hydroxyphenylethyl)-1,3,5-triazine, 1,3,5-tris(3,5-di-tert-butyl-4-hydroxy-phenylpropionyl)-hexahydro-1,3,5-triazine, 1,3,5-tris(3,5-dicyclohexyl-4-hydroxybenzyl)iso-cyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono- or poly-hydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, tri-ethylene glycol, pentaerythritol, tris(hydroxyethyl)isocyanurate, N,N'-bis (hydroxyethyl)ox-amide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)ox-amide, 3-thiaundecanol, 3-thiapentadecanol, trimethylhexanediol, trimethylolpropane, 4-hydroxymethyl-1-phospha-2,6,7-trioxabicyclo [2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl] propionyloxy)ethyl]oxamide (Naugard® XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenyl-amine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butyl-aminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylamino-methylphenol, 2,4'-diaminodiphenylmethane, 4,4'-diaminodiphenylmethane, N,N,N',N'-tetra-methyl-4,4'-diaminodiphenylmethane, 1,2-bis[(2-methylphenyl)amino]ethane, 1,2-bis(phenyl-amino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenyl-amines, a mixture of mono- and dialkylated nonyldiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene.

2. UV Absorbers and Light Stabilizers 2.1. 2-(2'-Hydroxyphenyl)benzotriazoles, for example 2-(2'-hydroxy-5'-methylphenyl)-benzo-triazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethyl butyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethyl benzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyl-oxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-meth-oxycarbonylethyl)phenyl)benzotriazole, 2-(3'-tert-butyl-2'-hydroxy-5'-(2-octyloxycarbonyl-ethyl)phenyl)benzotriazole, 2-(3'-tert-butyl-5'-[2-(2-ethylhexyloxy)carbonylethyl]-2'-hydroxy-phenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethyl benzyl)-phenyl]benzotriazole.

2.2. 2-Hydroxybenzophenones, for example the 4-hydroxy, 4-methoxy, 4-octyloxy, 4-decyl-oxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzo-ate, hexadecyl 3,5-di-tert-butyl-4-hydroxybenzoate, octadecyl 3,5-di-tert-butyl-4-hydroxybenzoate, 2-methyl-4,6-di-tert-butyl phenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, neopentyl tetra(α-cyano-β,β-di-phenylacrylate).

2.5. Nickel compounds, for example nickel complexes of 2,2'-thio-bis[4-(1,1,3,3-tetramethyl-butyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethyl piperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl- 2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexa-methylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydro-oxy-2-methylpropoxy)-4-octadecanoyloxy-2,2,6,6-tetramethylpiperidine, 5-(2-ethylhexanoyl)-oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis-[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)-amino)-s-triazine.

2.7. Oxamides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethyl phenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydro-oxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenyl hydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl)phosphite, trilauryl phosphite, trioctadecyl phosphite, distearylpentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:
Tris(2,4-di-tert-butylphenyl)phosphite (Irgafos®168, Ciba Specialty Chemicals Inc.), tris(nonylphenyl)phosphite,

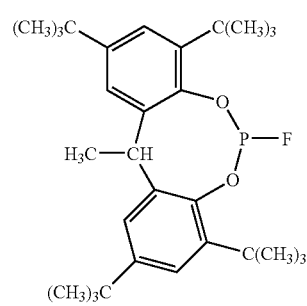

(A')

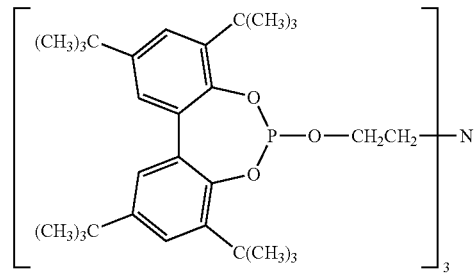

(B')

-continued (C')
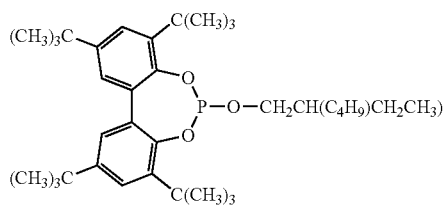

(D')
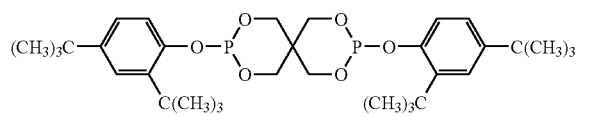

(E')
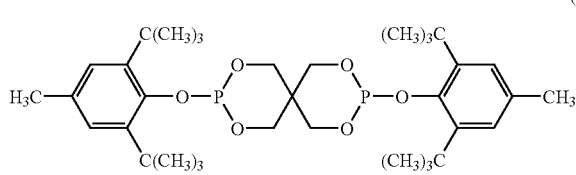

(F')
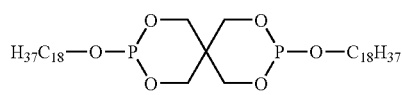

(G')
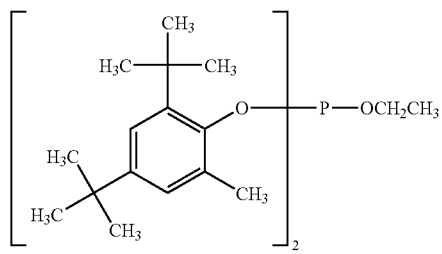

5. Hydroxylamines, for example N,N-dibenzylhydroxylamine, N,N-diethyl hydroxylamine, N,N-dioctylhydroxylamine, N,N-dilaurylhydroxylamine, N,N-ditetradecyl hydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkyl hydroxylamine derived from hydrogenated tallow amine.

6. Nitrones, for example, N-benzyl-alpha-phenylnitrone, N-ethyl-alpha-methylnitrone, N-octyl-alpha-heptyinitrone, N-lauryl-alpha-undecylnitrone, N-tetradecyl-alpha-tridecylnnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-hepta-decylnitrone, N-octadecyl-alpha-hexadecyl nitrone, nitrone derived from N,N-dialkylhydroxyl-amine derived from hydrogenated tallow amine.

7. Thiosynergists, for example dilauryl thiodipropionate, dimistryl thiodipropionate, distearyl thiodipropionate or distearyl disulfide.

8. Peroxide scavengers, for example esters of β-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethyl benzylidene)sorbitol, 1,3:2,4-di(paramethyl-dibenzyl idene)sorbitol, and 1,3:2,4-di(benzyl idene)sorbitol.

12. Fillers and reinforcing agents, for example calcium carbonate, silicates, glass fibres, glass beads, asbestos, talc, kaolin, mica, barium sulfate, metal oxides and hydroxides, car-bon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butyl benzofuran-2-one, 5,7-di-tert-butyl-3-[4-(2-stearoyloxy-ethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethyl phenyl)-5,7-di-tert-butyl benzofuran-2-one, 3-(2,3-dimethylphenyl)-5,7-di-tert-butylbenzofuran-2-one, 3-(2-acetyl-5-isooctylphenyl)-5-isooctyl-benzofuran-2-one.

The further additives are judiciously employed in amounts of 0.1-10% by weight, for example 0.2-5% by weight, based on the carrier material ii.

Another embodiment of this invention is the use of a 6,11-dihydroxy-naphthacene-5,12-dione in combination with a base or the use of a compound of formula (II) as defined above as a reversibly thermochromic colorant in a reversibly thermochromic system.

Preference is given to the use of a 6,11-dihydroxy-naphthacene-5,12-dione in combination with a base as defined above.

Another embodiment of this invention is a process for reversibly thermochromically coloring a carrier by applying thereto/incorporating therein a 6,11-dihydroxy-naphthacene-5,12-dione and a base or by applying thereto/incorporating therein a compound of formula (II) as defined above.

Preference is given to a process for reversibly thermochromically coloring a carrier by applying thereto/incorporating therein a 6,11-dihydroxy-naphthacene-5,12-dione in combination with a base as defined above.

A further embodiment of this invention is a compound of formula (I) or one the tautomers thereof as defined above, wherein at least one of $R_1$, $R_2$, $R_3$, $R_4$, $R_5$, $R_6$, $R_7$ and $R_8$ is or contains a sulfoxyl, a sulphonyl, an ester, an ether or an amide group, whereby if the sulphonyl group is phenylsulphonyl, at least two of $R_1$, $R_2$, $R_3$, $R_4$, $R_5$, $R_6$, $R_7$ and $R_8$ are phenylsulphonyl or at least two groups of $R_1$, $R_2$, $R_3$, $R_4$, $R_5$, $R_6$, $R_7$ and $R_8$ are carboxy or two adjacent groups of $R_1$, $R_2$, $R_3$, $R_4$, $R_5$, $R_6$, $R_7$ and $R_8$ form a 5- or 6-membered cyclic ring structure that is not maleic acid methyl imide or benzene or the compound of formula (I) is an oligomer or a polymer with the proviso that one of $R_2$, $R_3$, $R_6$ and $R_7$ cannot be $COOR_9$ with $R_9$ being isobutyl or 2-ethoxyethyl if the other seven substituents $R_1$-$R_8$ are hydrogen.

Another embodiment of this invention is a compound of formula (I) or one the tautomers thereof as defined above, wherein at least one of $R_1$, $R_2$, $R_3$, $R_4$, $R_5$, $R_6$, $R_7$ and $R_8$ is or contains a sulfoxyl, a sulphonyl, an ester, an ether or an amide group, whereby if the sulphonyl group is phenylsulphonyl, at least two of $R_1$, $R_2$, $R_3$, $R_4$, $R_5$, $R_6$, $R_7$ and $R_8$ are phenylsulphonyl or two groups of $R_1$, $R_2$, $R_3$, $R_4$, $R_5$, $R_6$, $R_7$ and $R_8$ are carboxy or two adjacent groups of $R_1$, $R_2$, $R_3$, $R_4$, $R_5$, $R_6$, $R_7$ and $R_8$ form a 5- or 6-membered cyclic ring structure that is not maleic acid methyl imide or benzene or the compound of formula (I) is an oligomer or a polymer.

The preferences for compounds of formula (I) of the reversibly thermochromic system outlined above are also eligible for these embodiments.

For example, one of $R_2$, $R_3$, $R_6$ and $R_7$ cannot be $COOR_9$ with $R_9$ being butyl (e.g. branched, in particular branched or linear), especially $R_9$ being unsubstituted or substituted $C_2$-$C_4$alkyl, in particular $R_9$ being unsubstituted or substituted $C_1$-$C_{30}$alkyl (e.g. cannot be $COOR_9$, in particular an ester group), if the other seven substituents $R_1$-$R_8$ are hydrogen.

For instance, $R_2$, $R_3$, $R_6$ and $R_7$ cannot be $COOR_9$ with $R_9$ being isobutyl (e.g. branched butyl, in particular branched or linear butyl) or 2-ethoxyethyl, in particular being unsubstituted or substituted $C_2$-$C_4$alkyl, especially being unsubstituted or substituted alkyl.

Of interest are substituents $R_2$, $R_3$, $R_6$ and $R_7$ not being COO—$R_9$, in particular not being an ester group.

For instance, the preferences for $R_2$, $R_3$, $R_6$ and $R_7$ outlined above are eligible for $R_1$-$R_8$.

For instance, at least one of $R_1$, $R_2$, $R_3$, $R_4$, $R_5$, $R_6$, $R_7$ and $R_8$ is or contains a sulfoxyl, a sulphonyl, an ether or an amide group, whereby if the sulphonyl group is phenylsulphonyl, at least two of $R_1$, $R_2$, $R_3$, $R_4$, $R_5$, $R_6$, $R_7$ and $R_8$ are phenylsulphonyl or two adjacent groups of $R_1$, $R_2$, $R_3$, $R_4$, $R_5$, $R_6$, $R_7$ and $R_8$ form a 5- or 6-membered cyclic ring structure that is not maleic acid methyl imide or benzene or the compound of formula (I) is an oligomer or a polymer.

For example, at least one of $R_1$, $R_2$, $R_3$, $R_4$, $R_5$, $R_6$, $R_7$ and $R_8$ is a sulfoxyl, a sulphonyl, an ester, an ether or an amide group, whereby if the sulphonyl group is phenylsulphonyl, at least two of $R_1$, $R_2$, $R_3$, $R_4$, $R_5$, $R_6$, $R_7$ and $R_8$ are phenylsulphonyl or at least two groups of $R_1$, $R_2$, $R_3$, $R_4$, $R_5$, $R_6$, $R_7$ and $R_8$ are carboxy or two adjacent groups of $R_1$, $R_2$, $R_3$, $R_4$, $R_5$, $R_6$, $R_7$ and $R_8$ form a 5- or 6-membered cyclic ring structure that is not maleic acid methyl imide or benzene or the compound of formula (I) is an oligomer or a polymer.

Of interest is when at least one of $R_1$, $R_2$, $R_3$, $R_4$, $R_5$, $R_6$, $R_7$ and $R_8$ is or contains a sulfoxyl group.

Also of interest is when at least one of $R_1$, $R_2$, $R_3$, $R_4$, $R_5$, $R_6$, $R_7$ and $R_8$ is or contains a sulphonyl group, whereby if the sulphonyl group is phenylsulphonyl, at least two of $R_1$, $R_2$, $R_3$, $R_4$, $R_5$, $R_6$, $R_7$ and $R_8$ are phenylsulphonyl. Preferably, none of $R_1$, $R_2$, $R_3$, $R_4$, $R_5$, $R_6$, $R_7$ and $R_8$ is or contains a phenyl sulphonyl.

Also of interest is when at least one of $R_1$, $R_2$, $R_3$, $R_4$, $R_5$, $R_6$, $R_7$ and $R_8$ is or contains an ester group. Preferably, at least two of $R_1$, $R_2$, $R_3$, $R_4$, $R_5$, $R_6$, $R_7$ and $R_8$ are or contain an ester group.

Also of interest is when at least one of $R_1$, $R_2$, $R_3$, $R_4$, $R_5$, $R_6$, $R_7$ and $R_8$ is or contains an ether group.

Also of interest is when at least one of $R_1$, $R_2$, $R_3$, $R_4$, $R_5$, $R_6$, $R_7$ and $R_8$ is or contains an amide group.

Also of interest is when at least two groups of $R_1$, $R_2$, $R_3$, $R_4$, $R_5$, $R_6$, $R_7$ and $R_8$ are carboxy. For instance, two groups of $R_1$, $R_2$, $R_3$, $R_4$, $R_5$, $R_6$, $R_7$ and $R_8$ are carboxy. For example, more than two groups of $R_1$, $R_2$, $R_3$, $R_4$, $R_5$, $R_6$, $R_7$ and $R_8$ are carboxy.

Also of interest is when two adjacent groups of $R_1$, $R_2$, $R_3$, $R_4$, $R_5$, $R_6$, $R_7$ and $R_8$ form a 5- or 6-membered cyclic ring structure that is not maleic acid methyl imide or benzene. For instance, the cyclic ring structure is a maleic acid anhydride. For example, the cyclic ring structure is a maleic acid imide. For instance, the cyclic structure is not a maleic acid imide. For example, the cyclic structure is not an aryl.

Also of interest is when the compound of formula (I) is an oligomer or a polymer.

The compounds described herein can be synthesized according to methods known in the art from known starting materials, see for example EP 0438376 A1. Some of the compounds described herein are commercially available.

Compounds of formula (II) can be prepared by mixing a) a compound of formula (I) or one of the tautomers thereof with b) a phosphinic or aminic base and reacting them together:
A) by melting the mixture at temperatures above the melting or softening points of the components and cooling the resulting salt to ambient temperature, or
B) by dissolving the components a) and b) in a convenient solvent, evaporating the solvent by heating or in vacuo, and cooling the residue to ambient temperature. Most solvents can be used for this purpose, as long as they are able to dissolve both components (but do not react with them) and can be evaporated afterwards. Some examples of solvents are dichloromethane, chloroform, methanol, ethanol, tetrahydrofuran, 1,4-dioxane, dimethyl formamide, acetone, acetonitrile, ethyl acetate and butyl acetate and mixtures thereof.

The reversibly thermochromic system or composition or compound of formula (II) as mentioned above may be used to indicate temperature changes in appliances or devices. The temperature change effects color changes which may be assessed by the human eye or by optical devices resulting in an effect signal.

An application of the reversibly thermochromic systems or compositions or compounds of formula (II) as described above is in the market of household appliances. For safety reasons there is often the need that the heated part of a certain device is evidenced through the appearance of a different and clearly distinguishable color.

For instance, in small appliances this is often desirable for kettles and percolators, toasters, indoor grills, slow cookers, food steamers, waffle makers, vacuum packaging systems, fryers, deep fryers, irons and rice cookers, where the high temperature may be indicated by the different color of a part of the item itself or of a label. The part or the label can be interchangeable, so that they can be changed with a new one available either in the original package or at the dealer, when the color change effect is no longer visible.

These thermochromic systems or compositions or compounds of formula (II) can be used in large appliances like cook-tops, dryers, ovens, space heaters, steam cleaners, dishwashers and washing machines.

The application of a reversibly thermochromic system or composition or compound of formula (II) is not limited to the incorporation into plastic parts of household appliances, but may find application also in many other contexts, for example:
  agricultural covers for light regulation purposes, in order to positively affect the development and harvesting of crops;
  inks in general, to be used in printing systems or in color-changing laminates, optionally as microencapsulated composition
  fibers and fabrics in general (both woven and non-woven), for apparel having fancy and fashionable features and for apparel and non-apparel purposes with functional characteristics, including brand protection;
  toys, including fabrics for clothes and molded objects to increase the appeal and the amusement from the article;
  food and non-food packaging, as temperature indicators ("too hot": article has to be refrigerated; or: "just the right temperature": article is at its best for consumption);
  promotional items such as hidden messages in tags, cards or labels; spoons, straws or stirrers for hot-cold drinks.

Percentages given are weight percentages unless otherwise stated. Percentages are given in percentages of the formulation, composition and/or combination unless otherwise stated.

PREPARATION EXAMPLES

Example 1

2-Dodecylsulfonyl-6,11-dihydroxy-naphthacene-5,12-dione

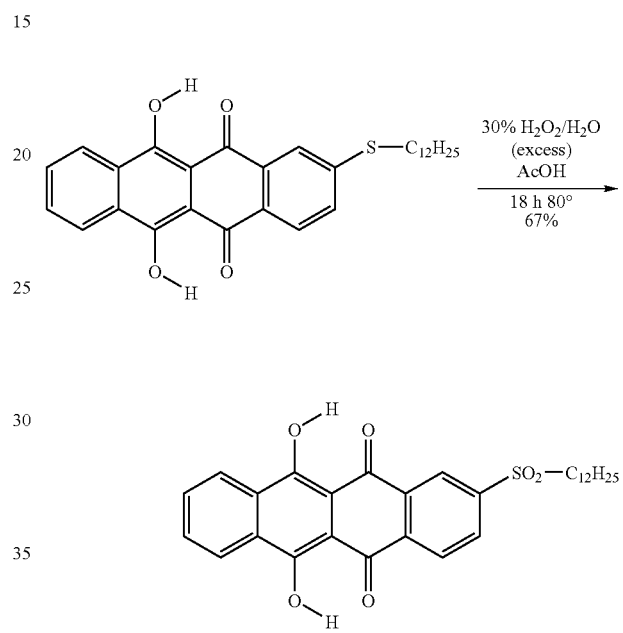

10 g (20 mmoles) of 2-n-dodecylthio-6,11-dihydroxy-naphthacene-5,12-dione is suspended in 250 ml glacial acetic acid. The mixture is stirred at 65°, and 64 ml of 30% hydrogen peroxide is slowly added in portions. The mixture is stirred at 80° for 18 h and then diluted with 2 L of water, stirred for 15 min, and filtered. The residue is washed with water and methanol, dried, and recrystallized from ethyl acetate yielding 7 g (67%) of red product, m.p. 185-186°.

Example 2

2,3-Bis(dodecylsulfonyl)-6,11-dihydroxy-naphthacene-5,12-dione

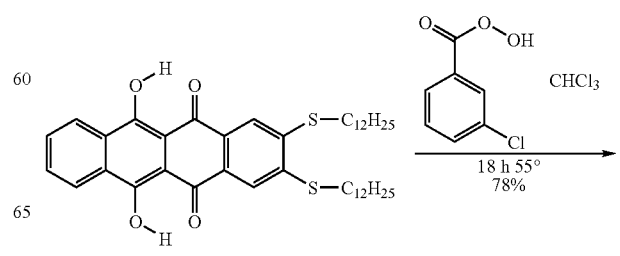

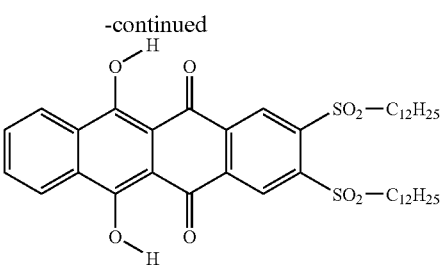

15 g (22 mmoles) of 2,3-bis(dodecylthio)-6,11-dihydroxy-naphthacene-5,12-dione is dissolved in 200 ml chloroform. 22.8 g (132.1 mmoles) of 3-chloro-perbenzoic acid is added in portions. The mixture is stirred at 55° for 18 h and then extracted with diluted potassium carbonate solution. The organic phases are washed with water, dried over sodium sulfate, and evaporated. The residue is recrystallized from ethyl acetate yielding 12.7 g (78%) of red product, m.p. 173-175°.

Example 2a

The starting material, 2,3-bis(dodecylthio)-6,11-dihydroxy-naphthacene-5,12-dione, is prepared as follows:

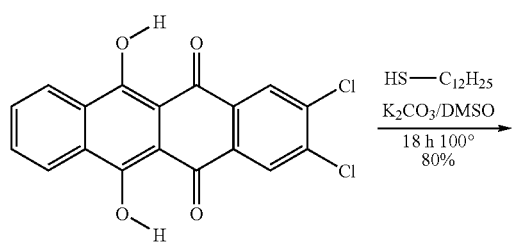

10 g (27.8 mmoles) of 2,3-dichloro-6,11-dihydroxy-naphthacene-5,12-dione, 100 ml dimethyl sulfoxide, 17 g (83.5 mmoles) dodecanethiol, and 19.24 g (139.2 mmoles) of potassium carbonate are stirred at 100° for 18 h. The mixture is diluted with water, stirred, and filtered. The residue is washed with water and methanol, dried, and recrystallized from hexane yielding 15.5 g (80%) of dark red product, m.p. 85-86°.

Similarly Prepared

Example 2b 2,3-Bis(octadecylthio)-6,11-dihydroxy-naphthacene-5,12-dione, m.p. 100-130°.

Example 2c 2,3-Bis(octadecylsulfonyl)-6,11-dihydroxy-naphthacene-5,12-dione, m.p. 152-156°.

Example 2d 2,3-Bis(phenylsulfonyl)-6,11-dihydroxy-naphthacene-5,12-dione, m.p. 305-310°.

Example 3

2,3,8,9-Tetrakis(n-dodecylsulfonyl)-6,11-dihydroxy-naphthacene-5,12-dione

This product is prepared from 2,3,8,9-tetrakis(n-dodecylthio)-6,11-dihydroxy-naphthacene-5,12-dione, similarly to Example 2, yielding 36% of a dark red product, m.p. 180-183°.

Example 4

2,3-Bis(4'-hydroxybutyl-sulfonyl)-6,11-dihydroxy-naphthacene-5,12-dione

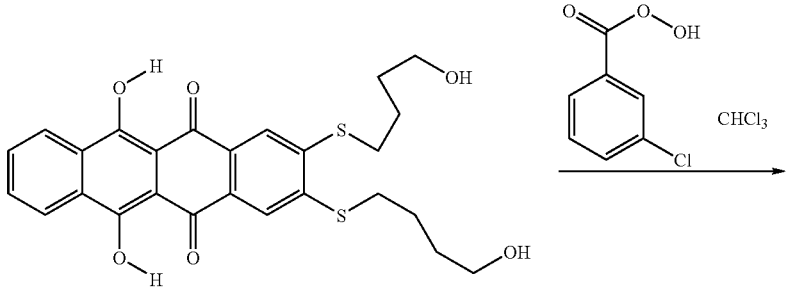

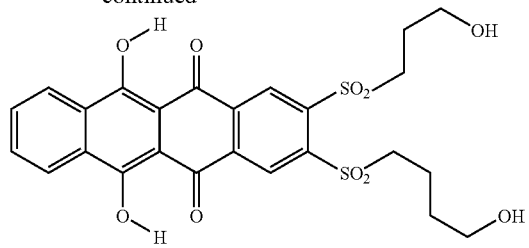

1 g (2 mmoles) of 2,3-bis(4'-hydroxybutylthio)-6,11-dihydroxy-naphthacene-5,12-dione is dissolved in 30 ml chloroform. 1.72 g (10 mmoles) of 3-chloro-perbenzoic acid is added in portions. The mixture is stirred at 62° for 5 h and then extracted with diluted aqueous potassium carbonate solution. The organic phases are washed with water, dried over sodium sulfate, and evaporated. The residue is recrystallized from dioxane yielding 0.64 g (57%) of red product, m.p. 203-206°.

Example 4a

The starting material, 2,3-bis(4'-hydroxybutylthio)-6,11-dihydroxy-naphthacene-5,12-dione, is prepared as follows:

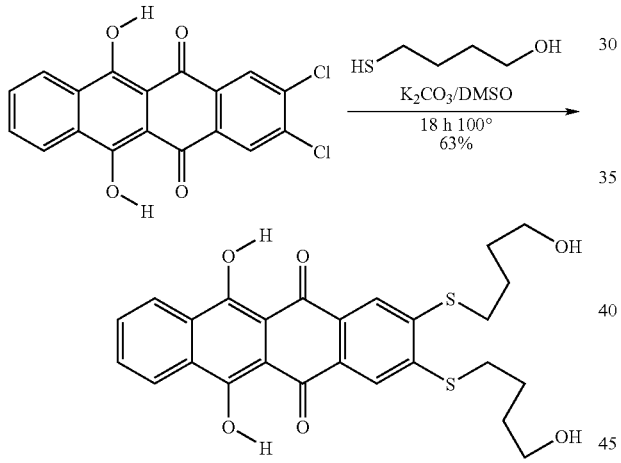

2.5 g (6.96 mmoles) of 2,3-dichloro-6,11-dihydroxy-naphthacene-5,12-dione, 20 ml dimethyl sulfoxide, 1.85 g (17.4 mmoles) of 4-mercaptobutanol, and 2.88 g (20.9 mmoles) of potassium carbonate are stirred at 100° for 18 h. The mixture is diluted with water, neutralized with hydrochloric acid, stirred, and filtered. The residue is washed with water, dried, and recrystallized from dioxane yielding 2.2 g (63%) of red product, m.p. 189-191°.

Similarly Prepared

Example 4b 2,3-Bis(2'-hydroxyethylthio)-6,11-dihydroxy-naphthacene-5,12-dione, m.p. 222-224°.

Example 4c 2,3-Bis(2'-hydroxyethylsulfonyl)-6,11-dihydroxy-naphthacene-5,12-dione, m.p. 277-280°.

Example 4d 2,3-Bis(6'-hydroxyhexylthio)-6,11-dihydroxy-naphthacene-5,12-dione, m.p. 129-130°.

Example 4e 2,3-Bis(6'-hydroxyhexylsulfonyl)-6,11-dihydroxy-naphthacene-5,12-dione, m.p. 209-211°.

Example 4f 2,3-Bis(6'-acetoxyhexylsulfonyl)-6,11-dihydroxy-naphthacene-5,12-dione: 1 g (1.6 mmoles) of 2,3-bis(6'-hydroxyhexylsulfonyl)-6,11-dihydroxy-naphthacene-5,12-dione (product of Example 4e) is acetylated by a mixture of 5 ml acetic acid, 0.36 g (3.55 mmoles) of acetic anhydride, and 2 drops of sulfuric acid, at 960 for 3.5 h. The mixture is diluted with water and filtered. The residue is washed with water and methanol and dried to give 1 g (89%) of 2,3-bis(6'-acetoxyhexylsulfonyl)-6,1'-dihydroxy-naphthacene-5,12-dione, m.p. 138-140°.

Example 5

2,3-Bis(3'-carboethoxy-propyl-1-sulfonyl)-6,11-dihydroxy-naphthacene-5,12-dione

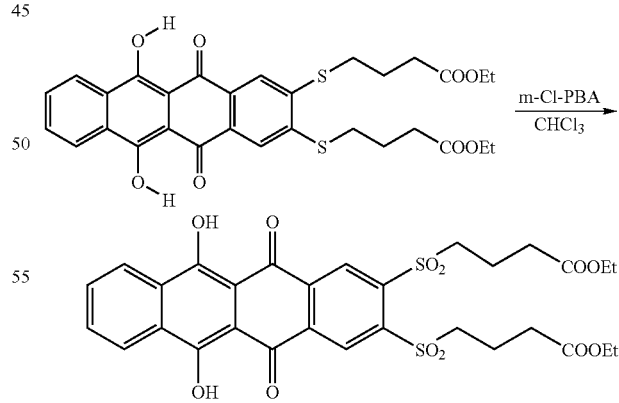

7 g (12 mmoles) of 2,3-bis(3'-carboethoxy-propyl-1-thio)-6,1-dihydroxy-naphthacene-5,12-dione are dissolved in 50 ml chloroform. 10.36 g (60 mmoles) of 3-chloro-perbenzoic acid is added in portions. The mixture is stirred at 56° for 2 h and then diluted with 500 ml water, and the chloroform is evaporated at 800 in vacuum. The precipitate is filtered and washed with hot water. The residue is recrystallized from methanol yielding 6.23 g (80%) of red product, m.p. 158-160°.

Example 5a

The starting material, 2,3-bis(3'-carboethoxy-propyl-1-thio)-6,11-dihydroxy-naphthacene-5,12-dione, is prepared as follows:

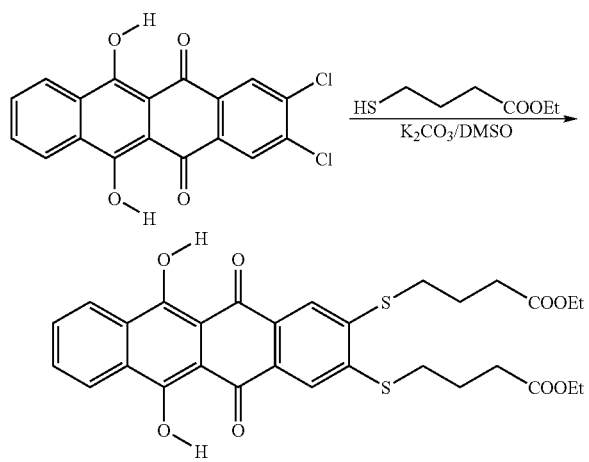

6.5 g (18.1 mmoles) of 2,3-dichloro-6,11-dihydroxy-naphthacene-5,12-dione, 50 ml dimethyl sulfoxide, 8 g (54.3 mmoles) of ethyl 3-mercaptopropionate, and 10 g (72.4 mmoles) of potassium carbonate are stirred at 100° for 18 h. The mixture is diluted with water, neutralized with hydrochloric acid, and extracted with chloroform and ethyl acetate. The organic extracts are washed with water, dried over sodium sulfate, and filtered over silica gel. The filtrate is evaporated, and the residue is recrystallized from chloroform/hexane yielding 7.38 g (70%) of red product, m.p. 129-132°.

Example 6

2-(2'-Ethylhexyl-1-oxycarbonyl-)-6,11-dihydroxy-naphthacene-5,12-dione

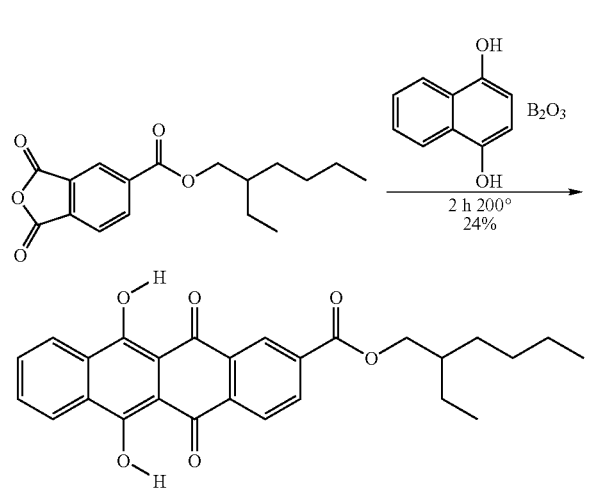

30 g (98.6 mmoles) of 4-(2'-ethyl-hexyl-1-oxycarbonyl-)-phthalic anhydride is mixed with 25.3 g (157.7 mmoles) of 1,4-dihydroxynaphthaline and 13.7 g (197.2 mmoles) of boron trioxide. The mixture is heated at 200° for 2 h. The solid residue is milled and triturated with boiling water. The precipitate is filtered, dried, and continuously extracted with hexane. The hexane extracts are partly concentrated to precipitate 10.7 g (24%) of red crystals, m.p. 155-158°.

The starting material, 4-(2'-ethyl-hexyl-1-oxycarbonyl-)-phthalic anhydride, is prepared as follows:

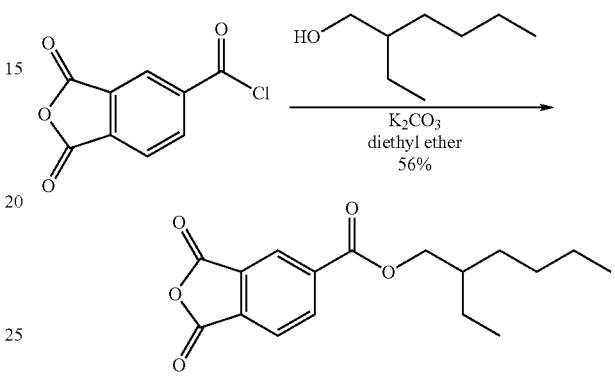

50 g (237 mmoles) of trimellitic anhydride chloride is suspended in 400 ml dry diethyl ether, 39.3 g (284 mmoles) of anhydrous potassium carbonate added, and 31 g (237 mmoles) of 2-ethyl-1-hexanol slowly added. The mixture is stirred at 25° for 3 d, diluted with water and extracted with diethyl ether. The extracts are dried with sodium sulfate and evaporated at 80°/0.3 mbar yielding 53.8 g of crude product. Distillation in a Kugelrohr apparatus at 140°/0.3 mbar gives 40.81 g (56%) of liquid 4-(2'-ethyl-hexyl-1-oxycarbonyl-)-phthalic anhydride.

Example 6a 6,11-Dihydroxy-naphthacene-5,12-dione-2,3-dicarboxylic acid dioctylester

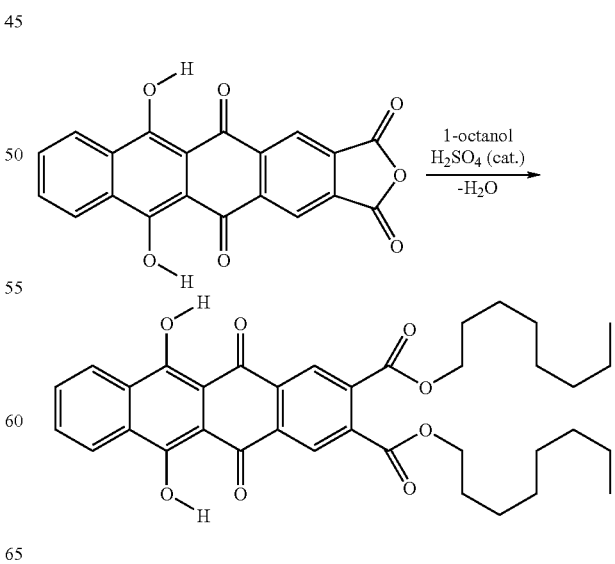

1.89 g (5.2 mmoles) of 6,11-dihydroxy-naphthacene-5,12-dione-2,3-dicarboxylic acid anhydride (product of example 9), 6.77 g (52 mmoles) of 1-octanol, and 0.2 g (2.08 mmoles) of 96% sulfuric acid are refluxed for 3 h with azeotropic removal of the reaction water. The mixture is kept at 25° for 18 h, then stirred with methanol and filtered. The precipitate is washed with water and dried in vacuo to give 2.58 g (81%) of red crystals, m.p. 95-96°.

Example 7

6,11-Dihydroxy-naphthacene-5,12-dione-2,3-dicarboxylic acid N-octylimide

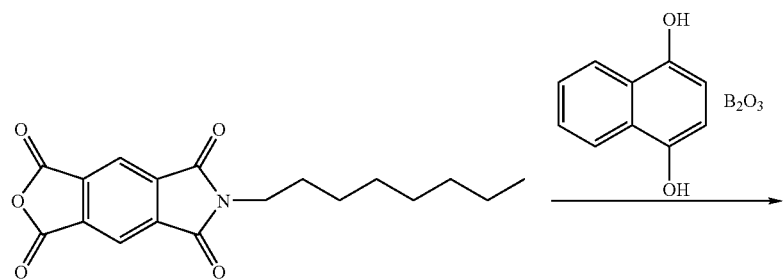

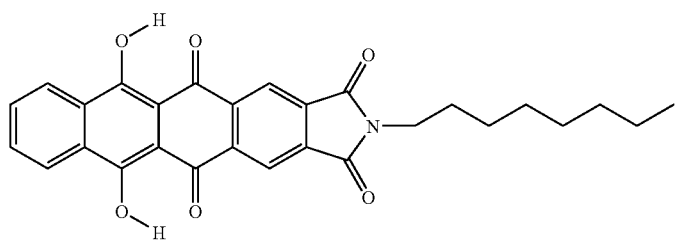

10 g (30.36 mmoles) of pyromellitic acid mono-anhydride-mono-N-octylimide is melted at 110°. 9.72 g (60.72 mmoles) of 1,4-dihydroxynaphthalene and 4.22 g (60.72 mmoles) of borontrioxide are added. The mixture is heated to 220° for 5 h, then cooled to 25°, and ground to a fine powder. This is washed with 2 N hydrochloric acid at 90°, then with hot water and methanol, and then dried. The dark red powder is triturated in chloroform and filtered through silica gel. The filtrate is concentrated partly, and the precipitate is filtered off, washed with chloroform/hexane (5:1), and dried, to yield 2.27 g (16%) of brownish crystals with metallic lustre, m.p. 253-255°.

Similarly Prepared

Example 7a 6,11-Dihydroxy-naphthacene-5,12-dione-2,3-dicarboxylic acid N-(2'-ethyl-hexyl)-imide; bronze crystals with metallic luster, m.p.: 245.5-246.5°.

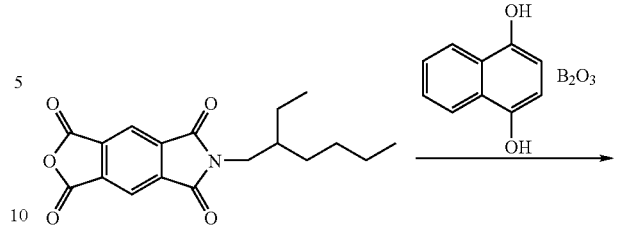

-continued

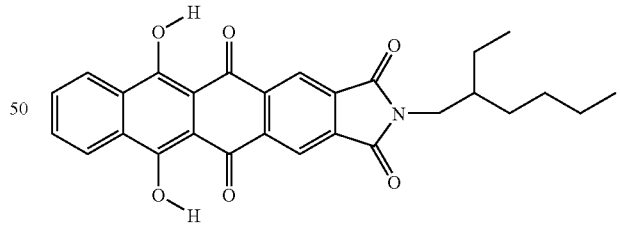

Example 7b 6,11-Dihydroxy-7,10-diphenyl-naphthacene-5,12-dione-2,3-dicarboxylic acid N-(2'-ethyl-hexyl)-imide; dark red crystals, m.p. 188-190°:

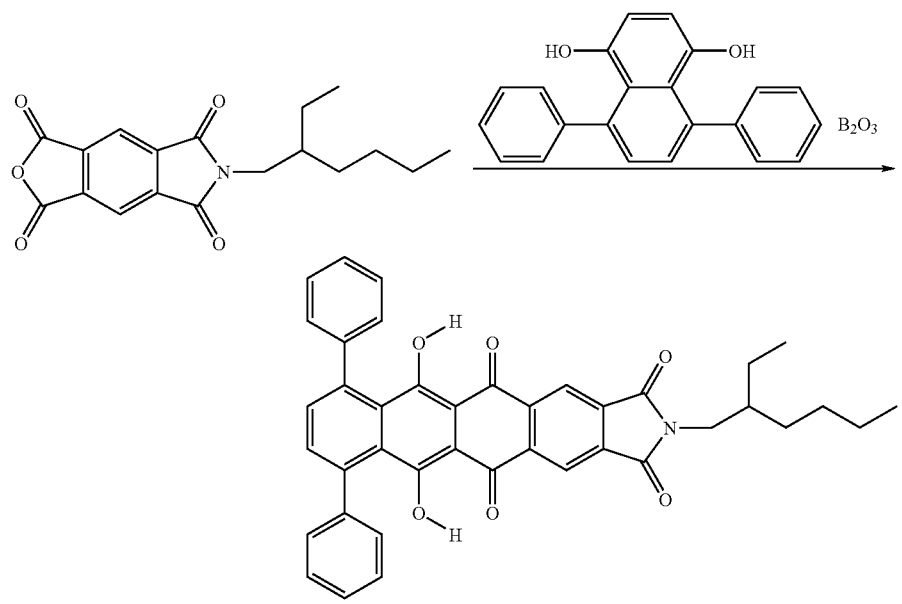

Example 8

6,11-Dihydroxy-naphthacene-5,12-dione-2,3-dicarboxylic acid

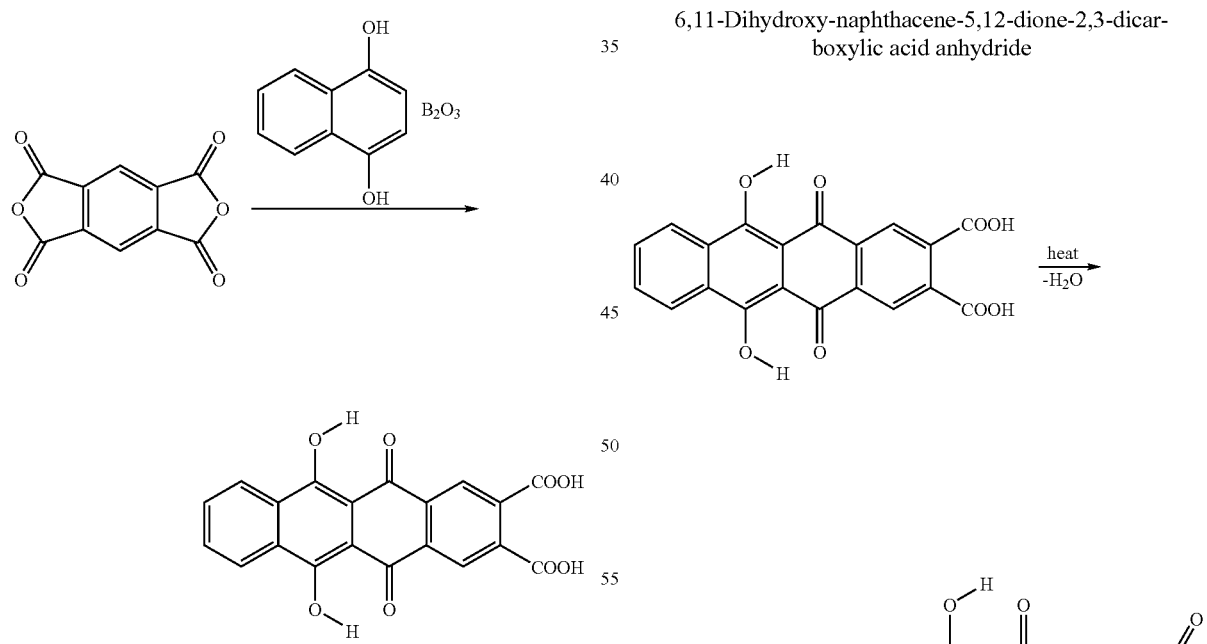

20 g (91.7 mmoles) of pyromellitic anhydride, 7.3 g (45.8 mmoles) of 1,4-dihydroxy-naphthalene, 6.4 g (91.7 mmoles) of borontrioxide, and 150 ml sulfolane are mixed and heated with stirring to 204° for 5 h, then cooled to 70°, and then mixed and stirred with hot water. The precipitate is filtered and washed with hot water and methanol, and then dried. The dark brown powder is extracted several times with hot dioxane. The filtrates are concentrated partly, allowed to stand at 25°, and the precipitate is filtered off, washed with dioxane, and dried at 90°/0.45 mbar, yielding 4.67 g (28%) of red crystals, m.p. >300° (dec.)°.

Example 9

6,11-Dihydroxy-naphthacene-5,12-dione-2,3-dicarboxylic acid anhydride

2.37 g (6.3 mmoles) of 6,11-dihydroxy-naphthacene-5,12-dione-2,3-dicarboxylic acid (product of Example 8) is heated to 250° at 0.84 mbar for 30 min. The bis-acid is thereby dehydrated to give 2.03 g (89%) of dark brown crystals, m.p. 405-408°.

Example 10

6,11-Dihydroxy-naphthacene-5,12-dione-2,3-dicarboxylic acid N-(2,6-diisopropyl-phenyl)-imide

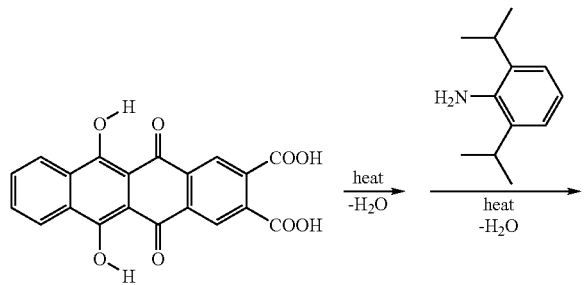

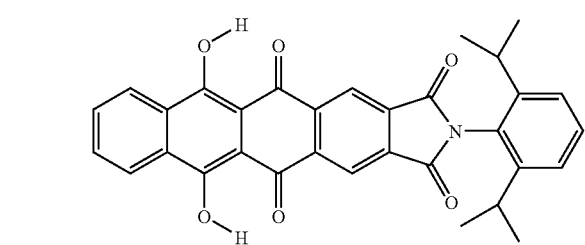

0.5 g (1.32 mmoles) of 6,11-Dihydroxy-naphthacene-5,12-dione-2,3-dicarboxylic acid (product of Example 8), 0.28 g (1.58 mmoles) of 2,6-diisopropylaniline, and 25 ml of o-dichlorobenzene are refluxed for 4 h with azeotropic removal of the reaction water. The mixture is filtered while hot, and the filtrate is kept at 25° for 18 h. The precipitate is washed with hot hexane and dried to give 0.35 g (51%) of red crystals, m.p. 328-330°.

Similarly Prepared

Example 10a 6,11-Dihydroxy-naphthacene-5,12-dione-2,3-dicarboxylic acid N-phenyl-imide from product of Example 8 and aniline; m.p.>400'; red-brown crystals.

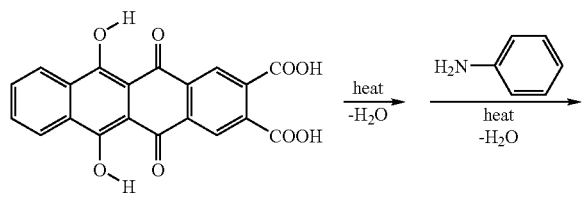

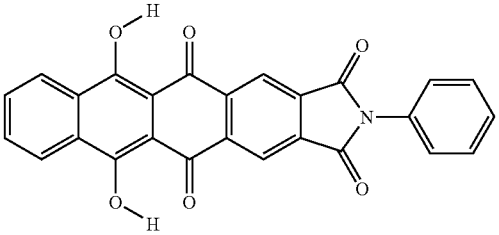

Example 10b 6,11-Dihydroxy-naphthacene-5,12-dione-2,3-dicarboxylic acid N-(2,6-dimethyl-phenyl-)imide from product of Example 8 and 2,6-dimethylaniline; m.p. 364-367°; red crystals.

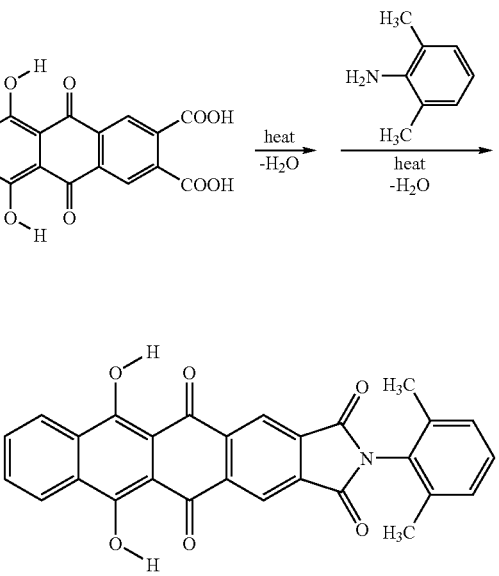

Example 10c 6,11-Dihydroxy-naphthacene-5,12-dione-2,3-dicarboxylic acid N-(2,6-diethyl-phenyl-)imide from product of Example 8 and 2,6-diethylaniline; m.p. 359-361°; red crystals.

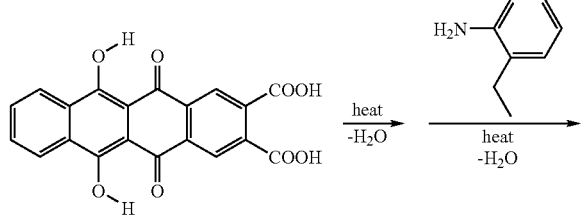

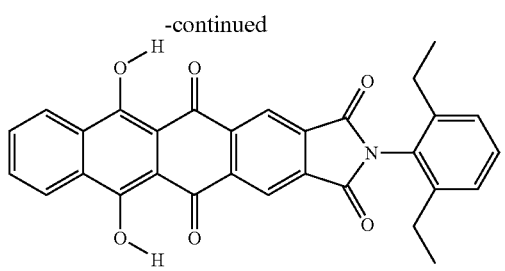

Example 10d 6,11-Dihydroxy-naphthacene-5,12-dione-2,3-dicarboxylic acid N-(1,1,3,3-tetra-methyl-butyl-)-imide

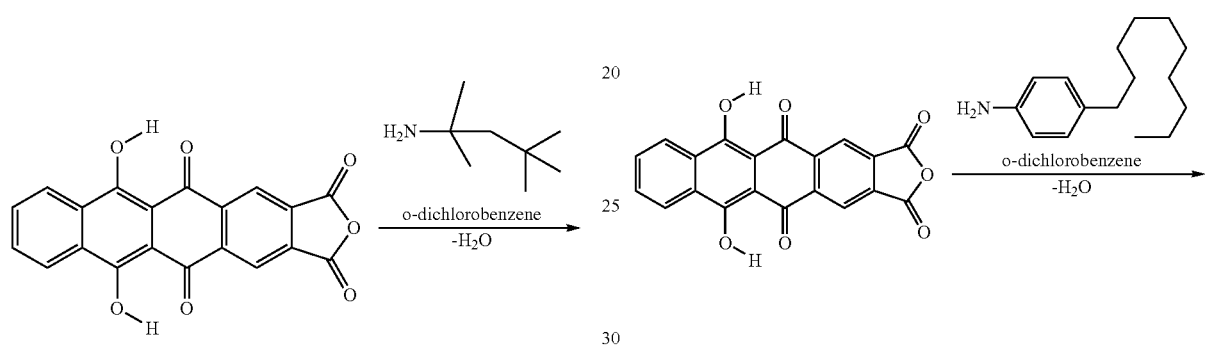

1 g (2.77 mmoles) of 6,11-dihydroxy-naphthacene-5,12-dione-2,3-dicarboxylic acid anhydride (product of Example 9), 0.54 g (84.16 mmoles) of 1,1,3,3-tetramethyl-1-butylamine, and 30 ml of o-dichlorobenzene are refluxed with azeotropic removal of the reaction water for 2 h.

The mixture is kept at 25° for 18 h, and the residue is filtered and washed with hot hexane to give 0.8 g (61%) of black shiny crystals, m.p. 268-272°.

Similarly Prepared

Example 10e 6,11-Dihydroxy-naphthacene-5,12-dione-2,3-dicarboxylic acid N-(4-decyl-phenyl)-imide from product of Example 9 and 4-decylaniline, m.p. 286-288°.

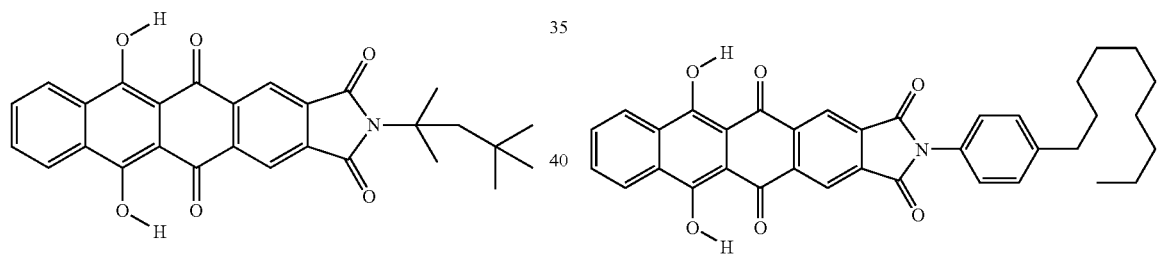

Example 11

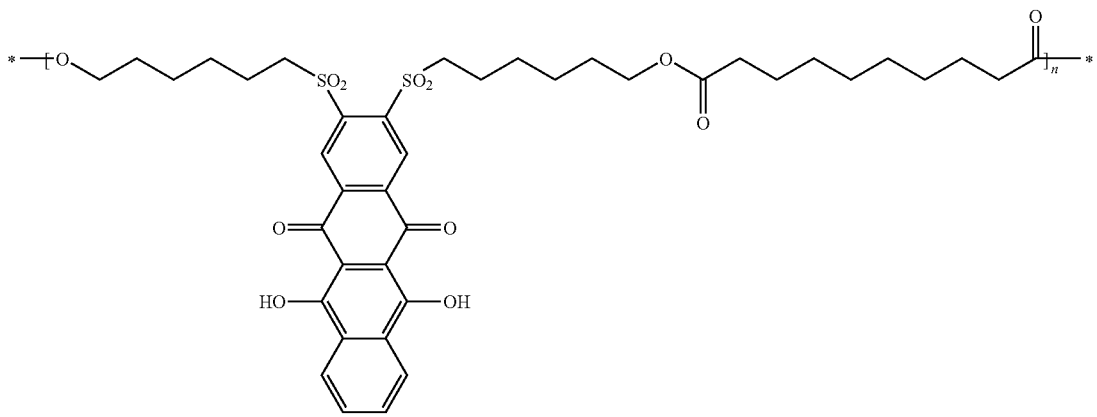

5 g (8 mmoles) of product of Example 4e, 2.3 g (8.9 mmoles) of diethylsebacate, 25 ml of 1,2-dichlorobenzene, 25 ml of xylene and 0.008 g of p-toluenesulfonic acid are put in a flask with Marcusson apparatus, condenser and mechanical stirrer. The mixture is warmed to 138° under current of nitrogen for 20 h. After that, 5 drops of sulphuric acid are added; the reaction goes on for further 10 h at 138°. After cooling to room temperature, the mixture is diluted with $CH_2Cl_2$ and washed with a solution of $KHCO_3$ in water. The organic layer is separated, dried, filtered and concentrated at rotavapor. 5.8 g of a dark red solid are obtained (yield: 90%). GPC analysis: $M_n$=1156, $M_w$=4010, $M_w/M_n$=3.5.

APPLICATION EXAMPLES

Formulation 1: 1.4 g of product of Example 2 corresponding to 0.2% of the total amount of the formulation and 21 g of poly[[6-[(1,1,3,3-tetramethylbutyl)amino]-1,3,5-triazine-2,4-diyl][(2,2,6,6-tetramethyl-4-piperidinyl)imino]-1,6-hexanediyl[2,2,6,6-tetramethyl-4-piperidinyl)imino]] (base 1; Chimassorb® 944), corresponding to 3.0%, are mixed in a turbomixer with 677.6 g of polypropylene powder (Basell Moplen HP500H) having a melt index of 1.8 (measured at 230° and 2.16 Kg).

The mixture is extruded at 190-230° to give polymer granules which are subsequently converted into plaques (1 mm thick), using a press-molding machine (Pasadena P210 C) operating at a maximum temperature of 240° and pressure of 20000 lb.

The same procedure was applied for formulations 2 and 3 with the amounts reported in the table below.

| Formulation | Product of Example 2 % | g | Base 1 % | g | PP Moplen HP500H g |
|---|---|---|---|---|---|
| 1 | 0.2 | 1.4 | 3.0 | 21 | 677.6 |
| 2 | 0.2 | 1.4 | 2.0 | 14.0 | 684.6 |
| 3 | 0.2 | 1.4 | 0.6 | 4.2 | 694.4 |

The same procedure is applied to formulation 4 containing: 0.9 g of product of Example 1 corresponding to 0.3% of the total amount of the formulation; 13.5 g of base 1 corresponding to 4.5% and 285.6 g of PP Moplen HP500H.

In order to induct a color change the plaques thus prepared are heated until their switching temperature. The change in color is assessed by means of a Minolta calorimeter CM-508d considering the CIEL*a*b* colorimetring space. On cooling the plaques go back to their initial color.

In the following table the results are reported:

| Formulation | Visual color At room temp. | At T > 100° | L* Before heating | L* After heating | a* Before heating | a* After heating | b* Before heating | b* After heating |
|---|---|---|---|---|---|---|---|---|
| 1 | Blue | Red | 20.4 | 25.4 | 8.4 | 7.3 | −14.8 | −0.8 |
| 2 | Blue | Red | 21.2 | 25.5 | 11.3 | 9.4 | −19.1 | −1.3 |
| 3 | Blue | Red | 21.5 | 25.8 | 6.1 | 8.1 | −8.7 | 2.0 |
| 4 | Violet | Red | 23.7 | 10.6 | 1.5 | 30.4 | 0.3 | 23.0 |

The changes of the colorimetric values show how efficiently the color of the plaques changes with temperature.

Additional formulations are prepared analogously:

Formulation 5: containing 0.35 g of product of Example 2 corresponding to 0.05% of the total amount of the formulation, 1.75 g of 1,6-hexanediamine,N,N'-bis(2,2,6,6-tetramethyl-4-piperidinyl)-polymer with 2,4,6-trichloro-1,3,5-triazine, reaction products with N-butyl-1-butanamine and N-butyl-2,2,6,6-tetramethyl-4-piperidinamine (base 2; Chimassorb® 2020), corresponding to 0.25% and 697.9 g of PP Moplen HP500H;

formulation 6: containing 0.35 g of product of Example 2 corresponding to 0.05% of the total amount of the formulation, 0.819 g of bis(2,2,6,6-tetramethyl-4-piperidyl)sebacate (base 3; Tinuvin® 770), corresponding to 0.117% and 698.831 g of PP Moplen HP500H;

formulation 7: containing 0.35 g of product of Example 2 corresponding to 0.05% of the total amount of the formulation, 0.798 g of bis(tridecyl)amine (base 4), corresponding to 0.114% and 698.852 g of PP Moplen HP500H.

Formulations 5-7 are extruded as described above and the granules are pressmolded in the same conditions as above to produce plaques (2 mm thick). The plaques are heated in order to induce the color change and their visual appearance is reported in the table below:

| Formulation | Visual color At room temperature | At T > 100° |
|---|---|---|
| 5 | Blue-Violet | Red |
| 6 | Blue | Red |
| 7 | Violet | Red |

Formulation 8: 10 mg of product of Example 2d and 150 mg of base 1 (see formulation 1 above) are dissolved in 1.0 g of a mixture of ethylene-vinylacetate polymer with hydrocarbon resins (hotmelt adhesive Nr. 6630.365 marketed by Migros Inc., 8031 Zürich, Switzerland) at 160°. Part of the clear red hot mixture is pressed between two glass plates resulting in a polymer spot which is blue at 25° and bright red at >100°. The heating/cooling cycle can be repeated >50 times without loss of the thermochromic characteristics.

Formulation 9: The formulation 8 is repeated using product of Example 4f instead of Example 2d, with the same result.

Formulation 10: The formulation 8 is repeated using product of Example 7 instead of Example 2d, with the same result.

Formulation 11: The formulation 8 is repeated using product of Example 7a instead of Example 2d, with the same result.

Formulation 12: The formulation 8 is repeated using product of Example 2 instead of Example 2d, with the same result.

Formulation 13: 10 mg of product of Example 4 and 150 mg of base 1 are dissolved in 2 ml of acetone. A piece of commercial lab filter paper is dropwise treated with a part of this solution. The solvent is evaporated in a warm air stream. The residual spot on the paper is dark blue at 25° and red at >80°. The heating/cooling cycle can be repeated >50 times without loss of the thermochromic characteristics.

When a piece of commercial cotton fabric is treated similarly with the above-mentioned solution a similar result is obtained after drying. The heating/cooling cycle can be repeated >50 times without loss of the thermochromic characteristics.

When the abovementioned solution is evaporated on a glass plate or a aluminum surface the residual stain is blue at 25° and red at >100°. The heating/cooling cycle can be repeated >50 times without loss of the thermochromic characteristics.

Formulation 14: Formulation 13 is repeated using product of Example 4e instead of Example 4 and dichloromethane instead of acetone as solvent, with similar results.

The invention claimed is:

1. A reversibly thermochromic system comprising
a) a 6,11-dihydroxy-naphthacene-5,12-dione and
b) a base with a molecular weight of at least 300,
wherein the base b) is an secondary or tertiary amine
where the secondary or tertiary amine is of formula $NHR_{26}R_{27}$ or $NHR_{26}R_{27}R_{28}$ where
$R_{26}$, $R_{27}$ and $R_{28}$ are independently $C_1$-$C_{30}$alkyl, $C_7$-$C_{12}$aralkyl, $C_2$-$C_{30}$alkenyl, $C_8$-$C_{12}$aralkenyl, $C_2$-$C_{30}$alkynyl or $C_8$-$C_{12}$aralkynyl, which are unsubstituted or substituted by one or more COO—$R_{21}$, CONR$_{21}$R$_{22}$, OCO—$R_{23}$, NR$_{21}$CO—$R_{23}$, NR$_{23}$R$_{21}$, O—$R_{23}$, S—$R_{23}$, SO—$R_{23}$ and/or S(=O)$_2$—$R_{23}$; or the aralkyl, aralkenyl and aralkynyl are substituted by $C_1$-$C_{30}$alkyl, $C_2$-$C_{30}$alkenyl and/or $C_2$-$C_{30}$alkynyl,
$R_{23}$ is $C_1$-$C_{30}$alkyl, $C_2$-$C_{30}$alkenyl, $C_2$-$C_{30}$alkynyl, $C_6$-$C_{10}$aryl, $C_7$-$C_{12}$aralkyl, $C_8$-$C_{12}$aralkenyl or $C_8$-$C_{12}$aralkynyl and $R_{21}$ and $R_{22}$ are independently H or as defined for $R_{23}$ or
the secondary or tertiary amine is of formula III

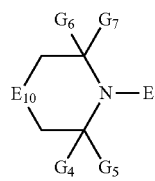

(III)

wherein $G_4$, $G_5$, $G_6$ and $G_7$ are independently methyl or ethyl,
E is hydrogen, $C_1$-$C_{18}$ alkyl or $C_3$-$C_{18}$alkenyl and
$E_{10}$ is a carbon atom which is unsubstituted or substituted by OH, =O or by one or two organic residues containing in total 1-500 carbon atoms,
wherein said reversibly thermochromic system demonstrates a reversibly thermochromic property.

2. A reversibly thermochromic system of claim 1, wherein component a) is a compound of formula (I) or one of the tautomers thereof

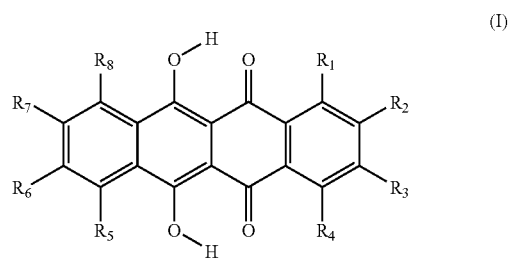

(I)

wherein
$R_1$, $R_2$, $R_3$, $R_4$, $R_5$, $R_6$, $R_7$ and $R_8$ independently are H, $C_1$-$C_{30}$alkyl, $C_7$-$C_{12}$aralkyl, $C_1$-$C_{30}$alkoxy, $C_1$-$C_{30}$alkylthio, $C_1$-$C_{30}$alkylsulfoxyl, $C_1$-$C_{30}$alkylsulfonyl, $C_2$-$C_{30}$alkenyl, $C_8$-$C_{12}$aralkenyl, $C_2$-$C_{30}$alkenyloxy, $C_2$-$C_{30}$alkenylthio, $C_2$-$C_{30}$ alkenylsulfoxyl, $C_2$-$C_{30}$alkenylsulfonyl, $C_2$-$C_{30}$alkynyl, $C_8$-$C_{12}$aralkynyl, $C_2$-$C_{30}$alkynyloxy, $C_2$-$C_{30}$alkynylthio, $C_2$-$C_{30}$alkynylsulfoxyl, $C_2$-$C_{30}$alkynylsulfonyl, $C_6$-$C_{10}$aryl, $C_6$-$C_{10}$aryloxy, $C_6$-$C_{10}$arylthio, $C_6$-$C_{10}$arylsulfoxyl, $C_6$-$C_{10}$arylsulfonyl, halogen, NO$_2$, CN, COO—$R_9$, OCO—$R_{10}$, CO—NR$_9$R$_{11}$ or NR$_{12}$CO—$R_{13}$, whereby the alkyl, alkenyl, alkynyl, aryl and aralkyl are substituted or unsubstituted,
or $R_2$, $R_3$, $R_6$ and/or $R_7$ are hydroxy;
or two adjacent groups of $R_1$, $R_2$, $R_3$, $R_4$, $R_5$, $R_6$, $R_7$ and $R_8$ form a 5- or 6-membered alicyclic or heterocyclic ring structure together with the two carbon atoms they are directly connected to;
or two of the substituents $R_1$, $R_2$, $R_3$, $R_4$, $R_5$, $R_6$, $R_7$ and $R_8$ are defined as follows:
one substituent is the group

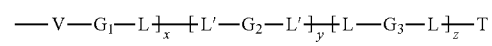

and the other substituent is the group

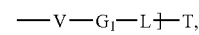

so the part of the one substituent with the open bracket and the part of the other substituent with the open bracket form together with the part of the molecule they are both attached to a monomer unit that is x times part in an oligomer or polymer;
$R_{10}$ and $R_{13}$ are independently $C_1$-$C_{30}$alkyl, $C_2$-$C_{30}$alkenyl, $C_2$-$C_{30}$alkynyl, $C_6$-$C_{10}$aryl, $C_7$-$C_{12}$aralkyl, $C_8$-$C_{12}$aralkenyl, $C_8$-$C_{12}$aralkynyl or an organic polymer, whereby the alkyl, alkenyl, alkynyl, aryl, aralkyl, aralkenyl and aralkynyl are substituted or unsubstituted;
$R_9$ is H or as defined for $R_{10}$;
$R_{11}$ and $R_{12}$ are independently H or $C_1$-$C_{30}$alkyl, $C_2$-$C_{30}$alkenyl, $C_2$-$C_{30}$alkynyl, $C_6$-$C_{10}$aryl, $C_7$-$C_{12}$aralkyl, $C_8$-$C_{12}$aralkenyl or $C_8$-$C_{12}$aralkynyl, whereby the alkyl, alkenyl, alkynyl, aryl aralkyl, aralkenyl and aralkynyl are substituted or unsubstituted;
V is independently CH$_2$, S, SO or SO$_2$;
G is $C_1$-$C_{30}$ alkylene;
L and L' are A or B; if L is A, then L' is B; if L is B, then L' is A;

A is O, S or $NR_{14}$;
$R_{14}$ is H, $C_1$-$C_{30}$alkyl, $C_2$-$C_{30}$alkenyl, $C_2$-$C_{30}$alkynyl, $C_6$-$C_{10}$aryl, $C_7$-$C_{12}$aralkyl, $C_8$-$C_{12}$aralkynyl or $C_8$-$C_{12}$aralkenyl;
B is CO;
$G_2$ is $C_1$-$C_{30}$alkylene; said alkylene is optionally interrupted by O, S, SO, $SO_2$, $NR_{14}$ or $G_2$ is one of the groups

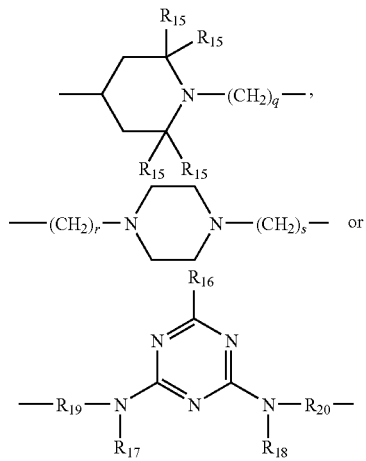

$R_{15}$ is H or $CH_3$;
q, r and s are independently integers from 1 to 20;
$R_{16}$ is $NH_2$, $NHR_{14}$ or

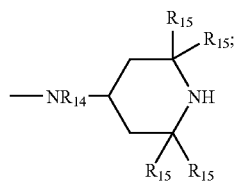

$R_{17}$ and $R_{18}$ are independently as defined for $R_{14}$ or

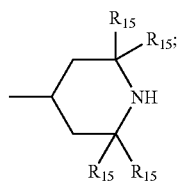

$R_{19}$ and $R_{20}$ are independently $C_1$-$C_{20}$alkylene;
$G_3$ has the same meanings as $G_2$;
T is H, if L is A; T is OH, if L=B;
x and y are independently integers from 1 to 20;
z is an integer from 0 to 20;
the substituted alkyl, alkenyl, alkynyl, aryl, aralkyl, aralkenyl and aralkynyl are substituted by halogen, hydroxy, nitro, cyano, COO—$R_{21}$, $CONR_{21}R_{22}$, OCO—$R_{23}$, $NR_{21}$CO—$R_{23}$, $NR_{21}R_{22}$, O—$R_{23}$ S—$R_{23}$SO—$R_{23}$ and/or S(=O)$_2$—$R_{23}$; or the substituted aryl, aralkyl, aralkenyl and aralkynyl are substituted by $C_1$-$C_{30}$alkyl, $C_2$-$C_{30}$alkenyl and/or $C_2$-$C_{30}$alkynyl;
$R_{23}$ is $C_1$-$C_{30}$alkyl, $C_2$-$C_{30}$alkenyl, $C_2$-$C_{30}$alkynyl, $C_6$-$C_{10}$aryl, $C_7$-$C_{12}$aralkyl, $C_8$-$C_{312}$aralkenyl or $C_8$-$C_{12}$aralkynyl; and
$R_{21}$ and $R_{22}$ are independently H or as defined for $R_{23}$.

3. A reversibly thermochromic system of claim 2, wherein $R_1$, $R_2$, $R_3$, $R_4$, $R_5$, $R_6$, $R_7$ and $R_8$ independently are H, $C_1$-$C_{30}$alkyl, $C_7$-$C_{12}$aralkyl, $C_1$-$C_{30}$alkoxy, $C_1$-$C_{30}$alkylthio, $C_1$-$C_{30}$alkylsulfoxyl, $C_1$-$C_{30}$alkylsulfonyl, $C_2$-$C_{30}$alkenyl, $C_8$-$C_{12}$aralkenyl, $C_2$-$C_{30}$alkenyloxy, $C_2$-$C_{30}$alkenylthio, $C_2$-$C_{30}$alkenylsulfoxyl, $C_2$-$C_{30}$alkenylsulfonyl, $C_2$-$C_{30}$alkynyl, $C_8$-$C_{12}$aralkynyl, $C_2$-$C_{30}$alkynyloxy, $C_2$-$C_{30}$alkynylthio, $C_2$-$C_{30}$alkynylsulfoxyl, $C_2$-$C_{30}$alkynylsulfonyl, $C_6$-$C_{10}$aryl, $C_6$-$C_{10}$aryloxy, $C_6$-$C_{10}$arylthio, $C_6$-$C_0$arylsulfoxyl, $C_6$-$C_{10}$arylsulfonyl, halogen, $NO_2$, CN, COO—$R_9$, OCO—$R_{10}$, CO—$NR_9R_{11}$ or $NR_{12}$CO—$R_{13}$, whereby the alkyl, alkenyl, alkynyl, aryl and aralkyl are substituted or unsubstituted,
or $R_2$, $R_3$, $R_6$ and/or $R_7$ are hydroxy:
or two adjacent groups of $R_1$, $R_2$, $R_3$, $R_4$, $R_5$, $R_6$, $R_7$ and $R_8$ form a 5- or 6-membered alicyclic or heterocyclic ring structure together with the two carbon atoms they are directly connected to, whereby the ring structure optionally contains one or two carbonyl groups and/or one or two hetero atoms, that are O, N, S, Se and/or P; the said ring structure is unsubstituted or substituted by $C_1$-$C_{30}$alkyl, $C_2$-$C_{30}$alkenyl, $C_2$-$C_{30}$alkynyl, unsubstituted or substituted $C_6$-$C_{10}$aryl, halogen, hydroxy, nitro, cyano, COO—$R_{21}$, $CONR_{21}R_{22}$, OCO—$R_{23}$$NR_{21}$CO—$R_{23}$$NR_{21}R_{22}$, O—$R_{23}$, S—$R_{23}$, SO—$R_{23}$, S(=O)$_2$—$R_{23}$ an organic poly- or oligomer, and/or an anellated 5- or 6-membered saturated or unsaturated ring structure that contains C and optionally one or two carbonyl groups and/or one or two hetero atoms, that are O, N, S, Se and/or P, the said anellated ring structure is unsubstituted or substituted by $C_1$-$C_{30}$alkyl, $C_2$-$C_{30}$alkenyl, $C_2$-$C_{30}$alkynyl, halogen, hydroxy, nitro, cyano, COO—$R_{21}$, $CONR_{21}R_{22}$, OCO—$R_{23}$, $NR_{21}COR_{23}$, $NR_{21}R_{22}$, O—$R_{23}$, S—$R_{23}$, SO—$R_{23}$, S(=O)$_2$—$R_{23}$, and/or anellated 5- or 6-membered saturated or unsaturated ring structure that contains C and optionally one or two carbonyl groups and/or one or two hetero atoms, that are O, N, S, Se and/or P;
or two of the substituents $R_1$, $R_2$, $R_3$, $R_4$, $R_5$, $R_6$, $R_7$ and $R_8$ are defined as follows:
one substituent is the group

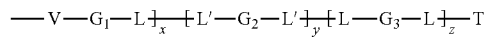

and the other substituent is the group

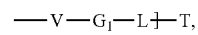

so the part of the one substituent with the open bracket and the part of the other substituent with the open bracket form together with the part of the molecule they are both attached to a monomer unit that is x times part in an oligomer or polymer; and
q, r and s are independently integers from 1 to 5.

4. A reversibly thermochromic system of claim 3, wherein $R_1$, $R_2$, $R_3$, $R_4$, $R_5$, $R_6$, $R_7$ and $R_8$ independently are H, $C_1$-$C_{30}$alkyl, $C_7$-$C_{12}$aralkyl, $C_1$-$C_{30}$alkoxy, $C_1$-$C_{30}$alkylthio, $C_1$-$C_{30}$alkylsulfoxyl, $C_1$-$C_{30}$alkylsulfonyl, $C_2$-$C_{30}$alkenyl, $C_8$-$C_{12}$aralkenyl, $C_2$-$C_{30}$alkenyloxy, $C_2$-$C_{30}$alkenylthio, $C_2$-$C_{30}$alkenylsulfoxyl, $C_2$-$C_{30}$alkenylsulfonyl, $C_2$-$C_{30}$alkynyl, $C_8$-$C_{12}$aralkynyl, $C_2$-$C_{30}$alkynyloxy, $C_2$-$C_{30}$alkynylthio, $C_2$-$C_{30}$alkynylsulfoxyl, $C_2$-$C_{30}$alkynylsulfonyl, $C_6$-$C_{10}$aryl, $C_6$-$C_{10}$aryloxy, $C_6$-$C_{10}$arylthio, $C_6$-$C_0$arylsulfoxyl, $C_6$-$C_{10}$arylsulfonyl, halogen, $NO_2$, CN, COO—$R_9$, OCO—$R_{10}$, CO—$NR_9R_{11}$ or $NR_{12}CO$—$R_{13}$, whereby the alkyl, alkenyl, alkynyl, aryl and aralkyl are substituted or unsubstituted, or $R_2$, $R_3$, $R_6$ and/or $R_7$ are hydroxy;

or $R_2$ and $R_3$ form together the group CO—O—CO or CO—$NR_{24}$—CO;

or $R_2$ and $R_3$ are defined as follows:
one substituent is the group

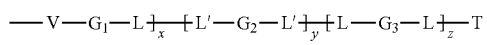

and the other substituent is the group

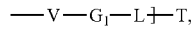

so the part of the one substituent with the open bracket and the part of the other substituent with the open bracket form together with the part of the molecule they are both attached to a monomer unit that is x times part in an oligomer or polymer;

$R_{24}$ is $C_2$-$C_{30}$ alkyl, $C_2$-$C_{30}$alkenyl, $C_2$-$C_{30}$alkynyl, $C_6$-$C_{10}$aryl, $C_7$-$C_{12}$aralkyl, $C_8$-$C_{12}$aralkenyl, $C_8$-$C_{12}$aralkynyl or

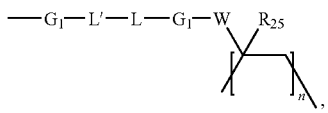

q is an integer from 2 to 4;
r and s are independently integers from 1 to 3;
W is $C_6$-$C_{10}$arylene, $C_1$-$C_{30}$alkylene, $C_1$-$C_{30}$alk-1-enylene, $NR_{11}$ or O; and
$R_{25}$ is H or $C_1$-$C_4$alkyl.

5. A reversibly thermochromic system of claim 4, wherein $R_1$, $R_2$, $R_3$, $R_4$, $R_5$, $R_6$, $R_7$ and $R_8$ independently are H, $C_1$-$C_{30}$alkyl, $C_7$-$C_{12}$aralkyl, $C_1$-$C_{30}$alkoxy, $C_1$-$C_{30}$alkylthio, $C_1$-$C_{30}$alkylsulfoxyl, $C_1$-$C_{30}$alkylsulfonyl, $C_6$aryl, $C_6$arylthio, $C_6$arylsulfoxyl, $C_6$arylsulfonyl, halogen, COO—$R_9$ or OCO—$R_{10}$, whereby the alkyl and aryl are substituted or unsubstituted, or $R_2$ and $R_3$ form together the group CO—O—CO or CO—$NR_{24}$—CO;

or $R_2$ and $R_3$ are defined as follows:
one substituent is the group

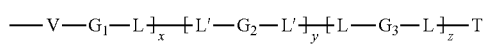

and the other substituent is the group

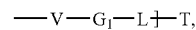

so the part of the one substituent with the open bracket and the part of the other substituent with the open bracket form together with the part of the molecule they are both attached to a monomer unit that is x times part in an oligomer or polymer;

$R_{10}$ is $C_1$-$C_{30}$alkyl or $C_6$aryl, whereby the alkyl and aryl is substituted or unsubstituted;
$R_9$ is H or as defined for $R_{10}$;
$R_{24}$ is unsubstituted or substituted $C_2$-$C_{30}$alkyl or $C_6$aryl;
V is $SO_2$;
$G_1$ is $C_2$-$C_{10}$alkylene;
L and L' are A or B; if L is A, then L' is B; if L is B, then L' is A;
A is O;
B is CO;
$G_2$ is $C_2$-$C_{10}$alkylene;
$G_3$ has the same meanings as $G_2$;
T is H, if L is A; T is OH, if L=B;
x and y are independently integers from 1 to 10;
z is an integer from 0 to 10;
the substituted alkyl and substituted aryl are substituted by hydroxy, COO—$R_{21}$, OCO—$R_{23}$ and/or O—$R_{23}$; or the aryl is substituted by $C_1$-$C_{15}$alkyl;
$R_{23}$ is $C_1$-$C_{15}$alkyl; and
$R_{21}$ is H or as defined for $R_{23}$.

6. A reversibly thermochromic system of claim 1, wherein the ratio of component a) to component b) is 2:1 to 1:100 by weight.

7. A reversibly thermochromic composition, comprising
i) a reversibly thermochromic system as defined in claim 1 and
ii) a carrier material.

8. A reversibly thermochromic composition of claim 7, wherein the ratio of component i) to component ii) is 1:10000 to 1:1.

9. A reversibly thermochromic composition of claim 7, comprising as carrier material ii) polymers, solvents and/or waxes.

10. A reversibly thermochromic composition of claim 7, comprising as carrier material ii) plastic articles, films, papers, fibers, solvents, waxes, coatings and/or inks.

11. A reversibly thermochromic composition of claim 7, comprising further additives selected from the group consisting of antioxidants, UV-absorbers, light stabilizers, metal deactivators, processing stabilizers, thiosynergists, peroxide scavengers, oxygen scavengers, basic co-stabilizers, nucleating agents, fillers, reinforcing agents, flameproofing agents and additional colorants, with the proviso that the additional colorants do not suppress and do not mask the thermochromic effect.

12. A reversibly thermochromic composition of claim 11, comprising as further additives phenolic antioxidants, aminic antioxidants, phosphites, phosphonites, hydroxylamines, nitrones, benzofuranones, indolinones, 2-(2-hydroxyphenyl)benzotriazoles, 2-hydroxybenzophenones, 2-(2-hydroxyphenyl)-1,3,5-triazines, oxamides, sterically hindered amines, pigments and/or dyes.

13. A process for reversibly thermochromically coloring a carrier by applying thereto/incorporating therein the reversibly thermochromic system of claim 1 comprising a 6,11-dihydroxy-naphthacene-5,12-dione and a base with a molecular weight of at least 300, wherein the base is an secondary or tertiary amine where the secondary or tertiary amine is of formula $NHR_{26}R_{27}$ or $NHR_{26}R_{27}R_{28}$ where $R_{26}$, $R_{27}$ and $R_{28}$ are independently $C_1$-$C_{30}$alkyl, $C_7$-$C_{12}$aralkyl, $C_2$-$C_{30}$alkenyl, $C_8$-$C_{12}$aralkenyl, $C_2$-$C_{30}$alkynyl or $C_8$-$C_{12}$aralkynyl, which are unsubstituted or substituted by one or more COO—$R_{21}$, $CONR_{21}R_{22}$, OCO—$R_{23}$, $NR_{21}$CO—$R_{23}$, $NR_{23}R_{21}$, O—$R_{23}$, S—$R_{23}$, SO—$R_{23}$ and/or $S(=O)_2$—$R_{23}$; or the aralkyl, aralkenyl and aralkynyl are substituted by $C_1$-$C_{30}$alkyl, $C_2$-$C_{30}$alkenyl and/or $C_2$-$C_{30}$alkynyl, $R_{23}$ is $C_1$-$C_{30}$alkyl, $C_2$-$C_{30}$alkenyl, $C_2$-$C_{30}$alkynyl, $C_6$-$C_{10}$aryl, $C_7$-$C_{12}$aralkyl, $C_8$-$C_{12}$aralkenyl or $C_8$-$C_{12}$aralkynyl and $R_{21}$ and $R_{22}$ are independently H or as defined for $R_{23}$ or the secondary or tertiary amine is of formula III

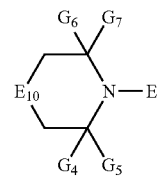

(III)

wherein $G_4$, $G_5$, $G_6$ and $G_7$ are independently methyl or ethyl,

E is hydrogen, $C_1$-$C_{18}$ alkyl or $C_3$-$C_{18}$alkenyl and $E_{10}$ is a carbon atom which is unsubstituted or substituted by OH, =O or by one or two organic residues containing in total 1-500 carbon atoms.

* * * * *